(12) United States Patent
Harwig et al.

(10) Patent No.: US 11,517,642 B2
(45) Date of Patent: Dec. 6, 2022

(54) PIEZOELECTRIC ACTIVE EMITTING DEVICE WITH IMPROVED AIR FLOW OUTPUT

(71) Applicant: S. C. JOHNSON & SON, INC., Racine, WI (US)

(72) Inventors: Jeff L Harwig, Franklin, WI (US); Nathan R. Westphal, Union Grove, WI (US); Kylie L. Levake, Union Grove, WI (US); Jason Stanbro, Sturtevant, WI (US); Daniel S McGrath, Gurnee, IL (US); Sebastian D Hasik, Antioch, IL (US); Scott D. Walter, Twin Lakes, WI (US); Jesse Richard, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 283 days.

(21) Appl. No.: 15/850,318

(22) Filed: Dec. 21, 2017

(65) Prior Publication Data
US 2019/0192717 A1 Jun. 27, 2019

(51) Int. Cl.
*A61L 9/03* (2006.01)
*A01M 1/20* (2006.01)
(Continued)

(52) U.S. Cl.
CPC ........... *A61L 9/037* (2013.01); *A01M 1/2072* (2013.01); *A61L 9/01* (2013.01); *A61L 9/032* (2013.01);
(Continued)

(58) Field of Classification Search
CPC ... A61L 9/01; A61L 9/015; A61L 9/02; A61L 9/032; A61L 9/037; A61L 9/04; A61L 9/122; A61L 9/127; A61L 9/14; A01M 1/2072; A01M 1/2077
USPC ..... 392/386, 394, 395, 396, 397; 239/102.1, 239/102.2, 302, 310, 318, 338, 368, 369, 239/370
See application file for complete search history.

(56) References Cited

U.S. PATENT DOCUMENTS

| 5,924,597 A | 7/1999 | Lynn |
| 6,347,992 B1 | 2/2002 | Durbin et al. |

(Continued)

FOREIGN PATENT DOCUMENTS

| EP | 1707889 A1 | 10/2006 |
| JP | 2006507196 A | 3/2006 |

(Continued)

OTHER PUBLICATIONS

Office Action from corresponding Japanese patent application No. 2020-531646, dated Jun. 2, 2022 (13 pages).

*Primary Examiner* — Justin C Dodson
(74) *Attorney, Agent, or Firm* — Quarles & Brady LLP

(57) ABSTRACT

A volatile material atomizing device comprises a housing having a fan, a fluid outlet, a plurality of air inlets and a plurality of air outlets. The plurality of air outlets are positioned at least partially around the fluid outlet. A fluid reservoir includes a wick and containing a volatile material. The fluid reservoir is disposed within the housing. An atomizing assembly is in fluid communication with the wick and positioned in the housing. The atomizing assembly is configured to dispense the volatile material out of the fluid outlet.

15 Claims, 17 Drawing Sheets

(51) Int. Cl.
*A61L 9/14* (2006.01)
*A61L 9/12* (2006.01)
*A61L 9/01* (2006.01)

(52) U.S. Cl.
CPC .............. *A61L 9/122* (2013.01); *A61L 9/127* (2013.01); *A61L 9/14* (2013.01); *A61L 2209/132* (2013.01); *A61L 2209/135* (2013.01)

(56) References Cited

U.S. PATENT DOCUMENTS

| | | | |
|---|---|---|---|
| 6,379,242 | B1 | 4/2002 | Wiseman, Sr. et al. |
| 6,722,529 | B2 | 4/2004 | Ceppaluni et al. |
| 7,490,815 | B2 | 2/2009 | Tollens et al. |
| 7,648,127 | B2 | 1/2010 | Cittadino |
| 7,824,627 | B2 | 11/2010 | Michaels et al. |
| 7,854,394 | B2 | 12/2010 | Powell et al. |
| 2004/0046053 | A1* | 3/2004 | Chen ......................... A61L 9/14 239/406 |
| 2005/0028254 | A1 | 2/2005 | Whiting |
| 2006/0011737 | A1* | 1/2006 | Amenos ............... A01M 1/2033 239/102.1 |
| 2012/0199206 | A1 | 8/2012 | Futa et al. |
| 2014/0097266 | A1 | 4/2014 | Habbel |
| 2014/0199206 | A1 | 7/2014 | Shen |
| 2014/0255012 | A1* | 9/2014 | Penman, Jr. ............ A61L 2/208 392/386 |
| 2015/0174595 | A1* | 6/2015 | Young ................... B05B 7/0012 261/78.2 |
| 2016/0106877 | A1* | 4/2016 | Albee ..................... A61L 9/122 239/418 |

FOREIGN PATENT DOCUMENTS

| | | | | |
|---|---|---|---|---|
| JP | 2008520395 A | 6/2008 | | |
| WO | 2000053301 A1 | 9/2000 | | |
| WO | 2012078973 A1 | 6/2012 | | |
| WO | 2015148203 A1 | 10/2015 | | |
| WO | WO-2015175527 A2 * | 11/2015 | .......... | A01M 1/2033 |
| WO | 2017015273 A1 | 1/2017 | | |
| WO | WO-2017/015273 A1 * | 1/2017 | .............. | A61L 9/01 |
| WO | 2017100070 A1 | 6/2017 | | |

* cited by examiner

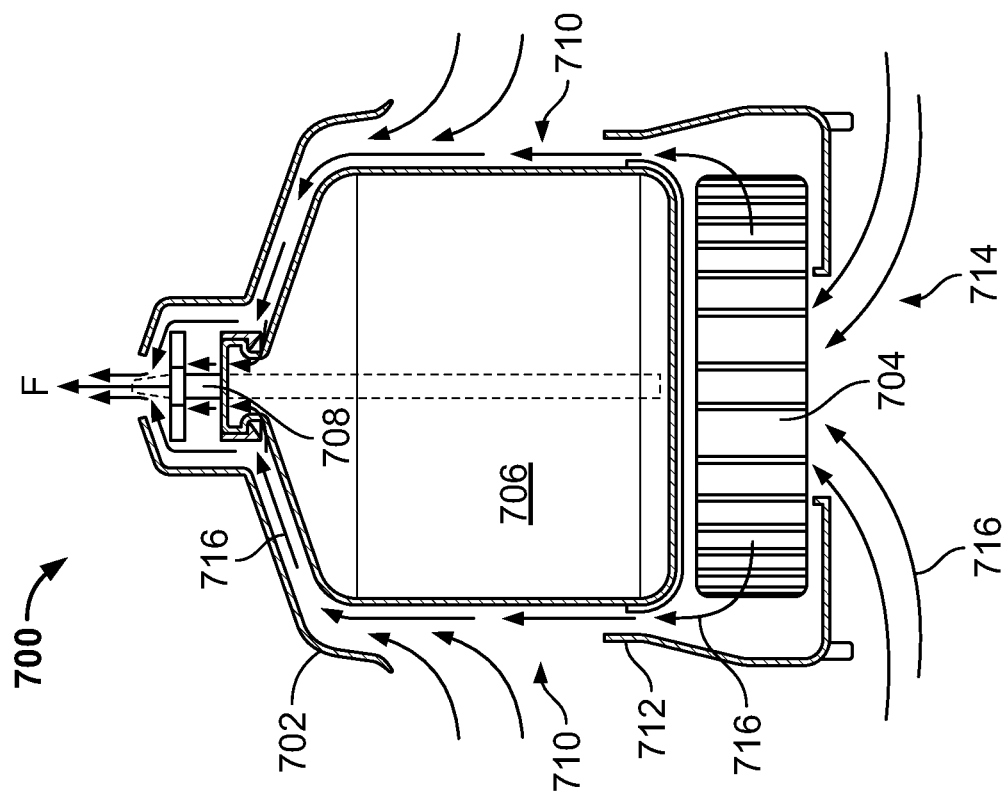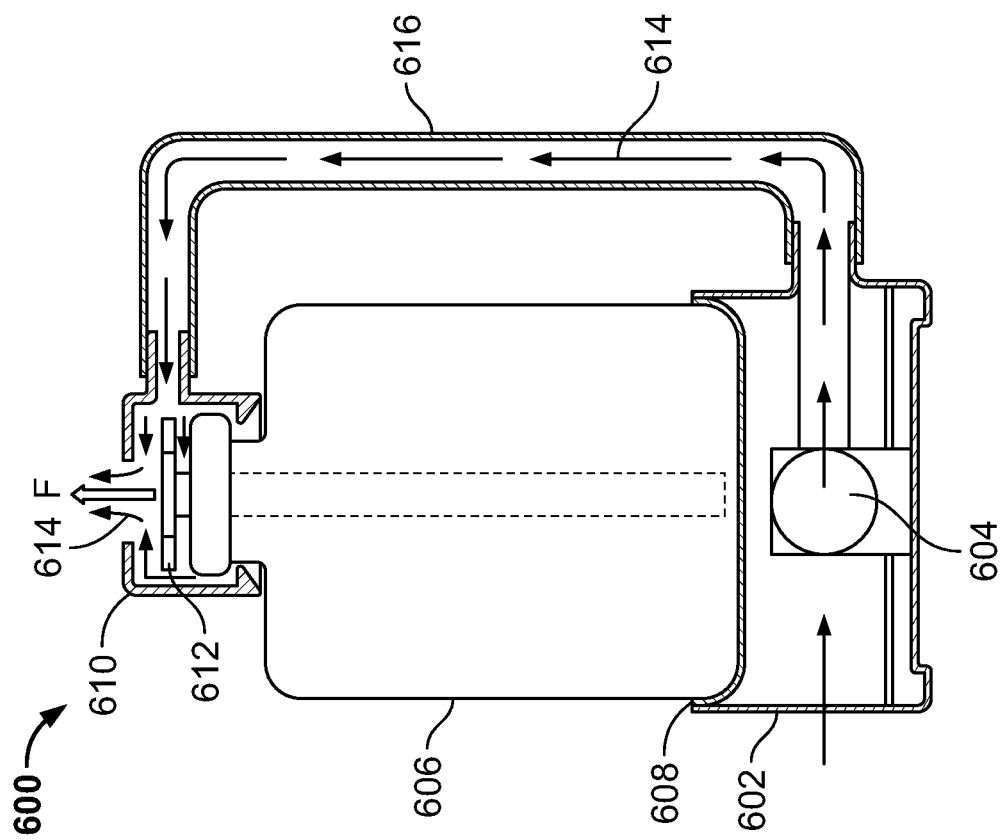

PIEZOELECTRIC ACTIVE EMITTING DEVICE WITH IMPROVED AIR FLOW OUTPUT

BACKGROUND

1. Field of the Disclosure

The present disclosure relates generally to active emitting devices and, more particularly, to piezoelectric active emitting devices for emission of volatile materials for long-lasting effects utilizing improved air flow techniques.

2. Description of the Background

A multitude of active material emitting devices exist in the marketplace. Many of such devices are passive devices that require only ambient air flow to disperse the liquid active material therein. Other devices are battery-powered or receive household power via a plug. A cord may be coupled between the plug and the device, or the plug may be mounted directly on the device.

Various means for dispensing active materials from emitting devices are also known in the art. For example, some emitting devices include a heating element for heating an active material to promote vaporization thereof. Other emitting devices employ a fan to generate air flow to direct active material out of the emitting device into the surrounding environment. In another type of emitting device, active material may be emitted from the device using a bolus generator that develops a pulse of air to eject a scent ring. Still other emitting devices utilize an ultrasonic transducer to break up an active material into droplets that are ejected from the device.

Vibratory-type liquid atomization devices are described in Martin et al. U.S. Pat. No. 6,341,732, Helf et al. U.S. Pat. No. 6,706,988, Helf et al. U.S. Pat. No. 6,896,193, Sipinski U.S. Pat. No. 7,455,245, and Martens, III et al. U.S. Pat. No. 7,775,459, all of which are assigned to the assignee of the present application. These patents disclose devices comprising a piezoelectric actuating element coupled to a liquid atomization plate. The piezoelectric actuating element vibrates the liquid atomization plate in response to alternating electrical voltages applied to the actuating element. The vibration of the plate causes atomization of a liquid supplied by a liquid delivery system. An electrical circuit is provided to supply the alternating electrical voltages to conductive elements that are in electrical contact with opposite sides of the actuating element. The conductive elements may also serve to support the actuating element and the liquid atomization plate in a housing that contains the device.

However, with atomization devices, a potential problem is that the atomized liquid droplets can settle back onto the device, and/or onto surfaces around the device, before they completely evaporate. This problem can be of particular concern, for example, with respect to insect control or air-freshening liquid formulations because such formulations often contain strong solvents that are harmful to surfaces, especially surfaces with fine lacquered wood finishes. Consumers often place liquid atomizing devices on such surfaces (e.g., on wooden furniture such as a table or a dresser), and when atomized liquid droplets fail to evaporate, and instead settle down onto the adjacent surfaces, the droplets can cause the finish on the surfaces to be damaged, among other unwanted effects.

To address this concern, changing the character of the dispensed liquid has been suggested. For example, the specific formulation of the dispensed liquid might be altered so that the liquid will not act as a furniture-stripping agent if it comes in contact with a finished wooden surface. This approach, however, can limit the selection of liquid components that can be used, especially the selection of usable fragrance components.

But even when the particular composition of the liquid formulation in a device is not necessarily damaging to a given surface, the accumulation of droplets on a surface can still be bothersome. For example, a plastic surface or a glass surface that does not react with the liquid formulation must still be cleaned by the user of the device after droplets have collected on that surface. As another example, a particular liquid formulation might not actually harm an area of carpet fibers or a fabric surface, but it could still be a nuisance due to being absorbable into the carpet or fabric.

Also of concern is that droplets can settle back onto the liquid atomizing device itself, presenting a nuisance and/or adversely affecting further atomization and efficient dispersion, such as by clogging the orifices through which the atomized liquid droplets are ejected into the air.

Accordingly, in a liquid atomizing device, there is a need to minimize the amount of atomized liquid droplets that fail to evaporate fully before settling down on the device and/or surrounding surfaces. The prior art fails to adequately teach suitable improvements for minimizing the amount of atomized liquid droplets that settle on the device and/or its surrounding surfaces by increasing the evaporation rate of dispensed droplets, in the manners set forth below.

SUMMARY

According to one illustrative embodiment, a volatile material atomizing device includes a housing having a fan, a fluid outlet, a plurality of air inlets and a plurality of air outlets. The plurality of air outlets are positioned at least partially around the fluid outlet. A fluid reservoir containing a volatile material is disposed within the housing. An atomizing assembly is in fluid communication with the containerss and positioned in the housing. The atomizing assembly is configured to dispense the volatile material out of the fluid outlet.

According to another illustrative embodiment, a volatile material atomizing device includes a housing having a fan, a fluid outlet, at least one air inlet, and a plurality of air outlets positioned at least partially around the fluid outlet. A fluid reservoir is positioned within the housing. The fluid reservoir includes a wick and contains a volatile material comprising a water-based fragrance composition. An atomizing assembly is in fluid communication with the wick and positioned in the housing. The atomizing assembly is configured to dispense the volatile material out of the fluid outlet. The atomizing assembly emits volatilized water-based fragrance composition out the fluid outlet and the fan produces an airflow out the air outlets to at least partially surround the volatilized water-based fragrance composition to carry the volatilized water-based fragrance composition up and away from the atomizing device.

According to a further illustrative embodiment, a volatile material atomizing device includes a housing having a lower portion and a top cover. A fluid outlet is formed in the top cover and a plurality of air outlets are formed at least partially around the fluid outlet. A fluid reservoir is disposed within the housing. The fluid reservoir includes a wick and contains a volatile material comprising a water-based fragrance composition. A fan is positioned within the housing and configured to draw air into the housing through at least one air inlet and create an airflow of at least 4 cfm out of the plurality of air outlets. An atomizing assembly is positioned within the housing and in fluid communication with the wick of the fluid reservoir. The atomizing assembly is configured to create a mist of fluid particles that dispense out of the fluid outlet. The airflow out of the plurality of air outlets and the mist dispensing out of the fluid outlet mix outside the housing above the top cover.

BRIEF DESCRIPTION OF THE DRAWINGS

FIG. 21 is a cross-sectional view of a sixth embodiment of an exemplary piezoelectric active emitting device that may embody the principles of the present disclosure; and FIG. 22 is a cross-sectional view of a seventh embodiment of an exemplary piezoelectric active emitting device that may embody the principles of the present disclosure.

Other aspects and advantages of the present disclosure will become apparent upon consideration of the following detailed description, wherein similar structures have like or similar reference numerals.

DETAILED DESCRIPTION

Figure 1:
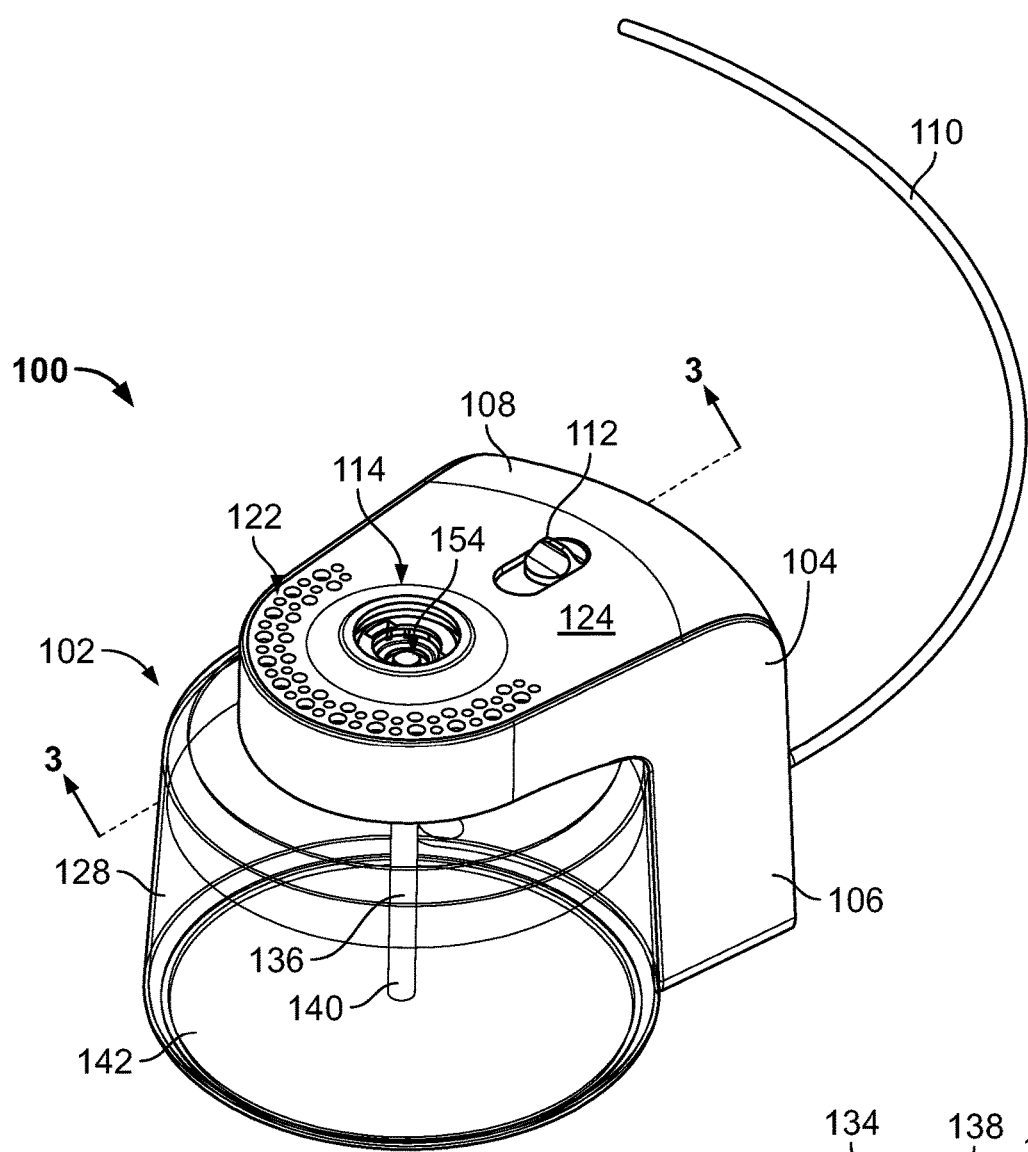
FIG. 1 is a top, front, and right side perspective view of a first embodiment of an exemplary piezoelectric active emitting device that may embody the principles of the present disclosure.

The present disclosure is directed to piezoelectric active emitting devices for emission of volatile materials for long-lasting effects utilizing improved air flow techniques. While the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Referring to the drawings, FIGS. 1-6 depict a first exemplary atomizing device 100, which includes a fluid reservoir 102. The atomizing device 100 includes a housing 104 comprising a base 106 and a top cover 108. The emitting device 100 includes an electrical connection 110. It is contemplated that the electrical connection may take any of the forms known to one having skill in the art. For example, in some embodiments, the connection may include a plug (not shown) configured to connect to standard electrical receptacles. Alternatively, in a different embodiment, the electrical connection may include a USB connection for connecting to a computer or other USB receptacle equipped device to receive power. Some exemplary embodiments may be configured to include batteries to power the atomization device and/or to provide a back-up power source.

Figure 3:
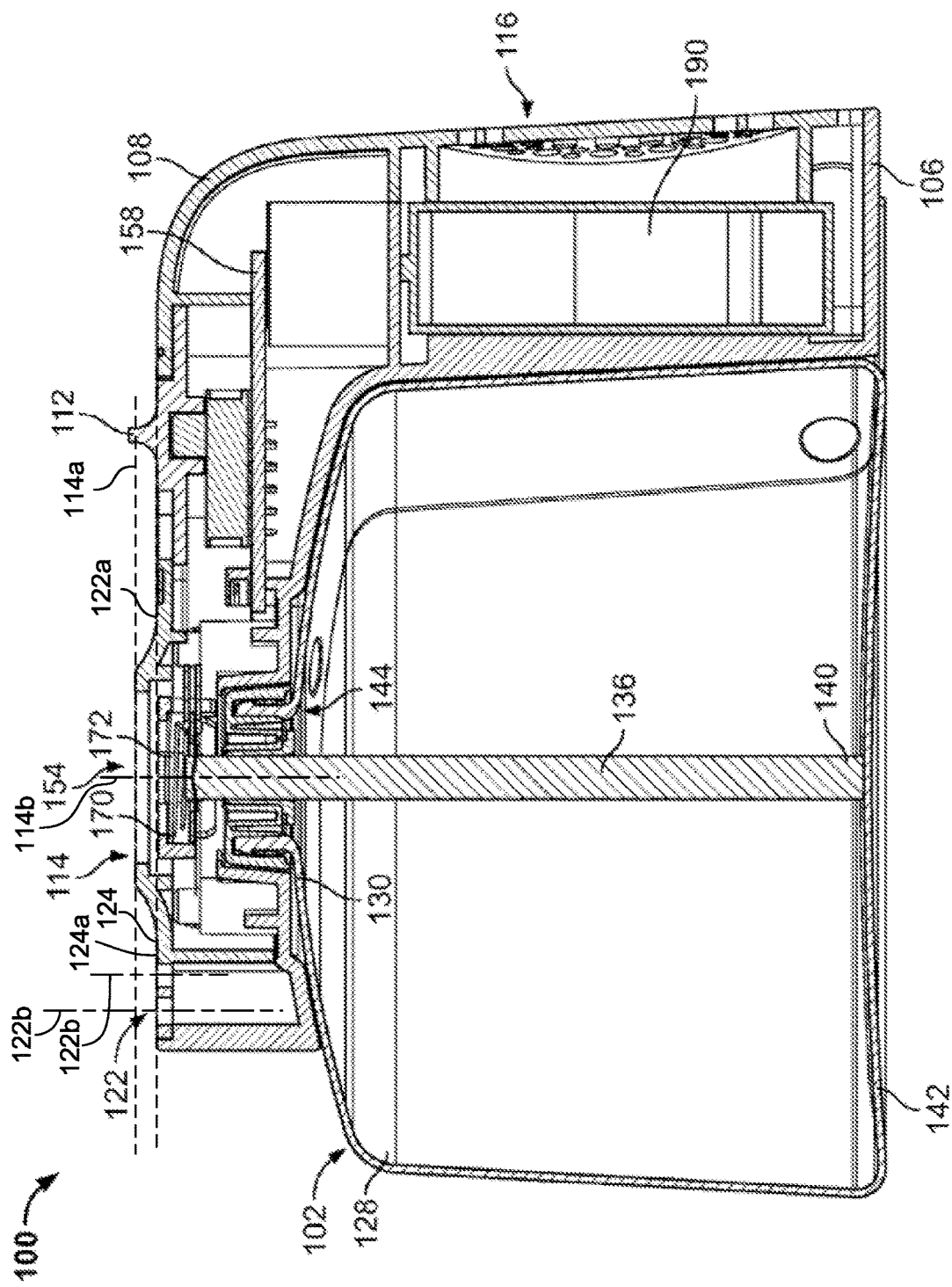
FIG. 3 is a cross-sectional view of the device of FIG. 1 generally taken along the lines 3-3 of FIG. 1.
Figure 4:
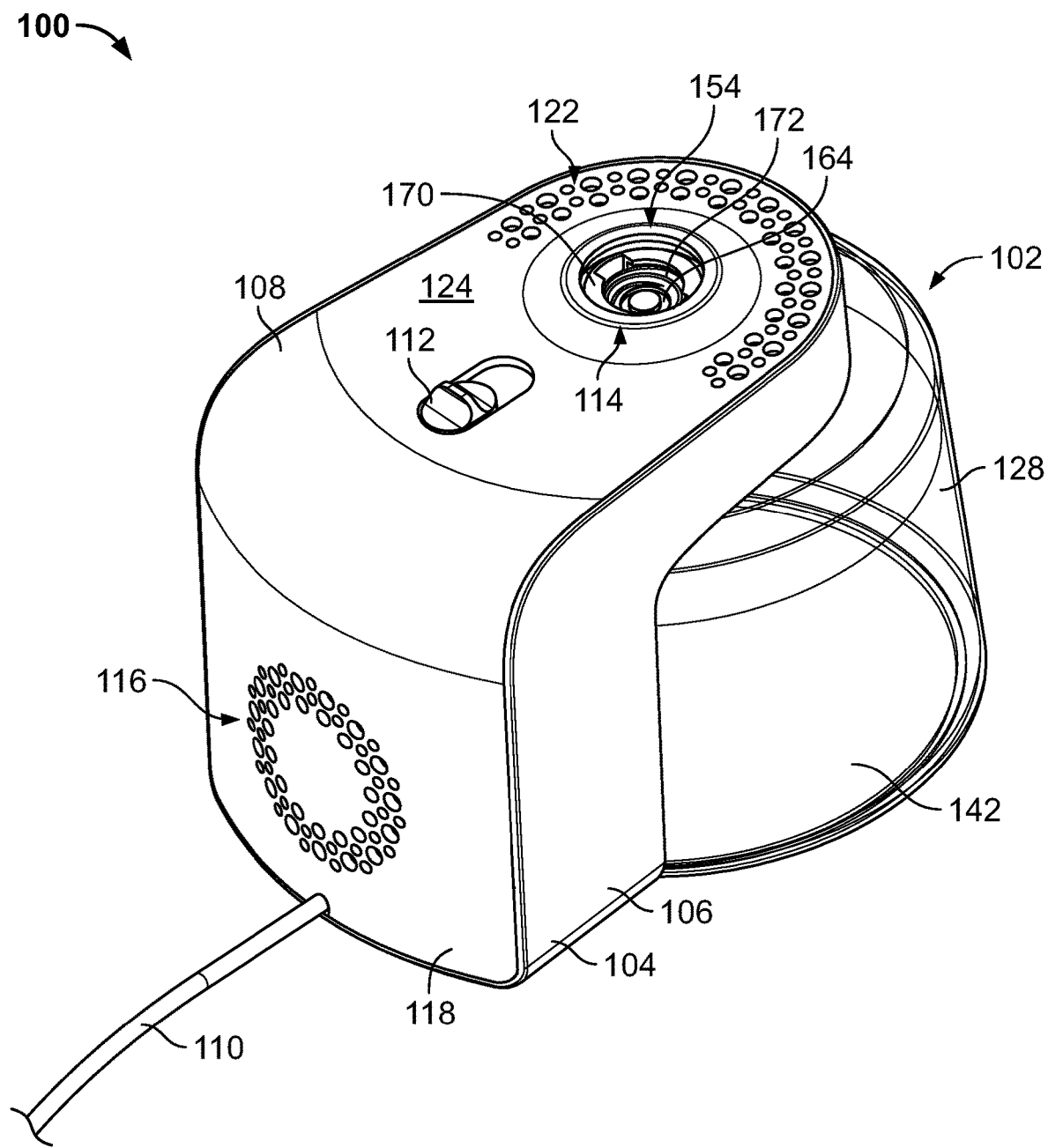
FIG. 4 is a top, rear, and left side perspective view of the device of FIG. 1.
Figure 5:
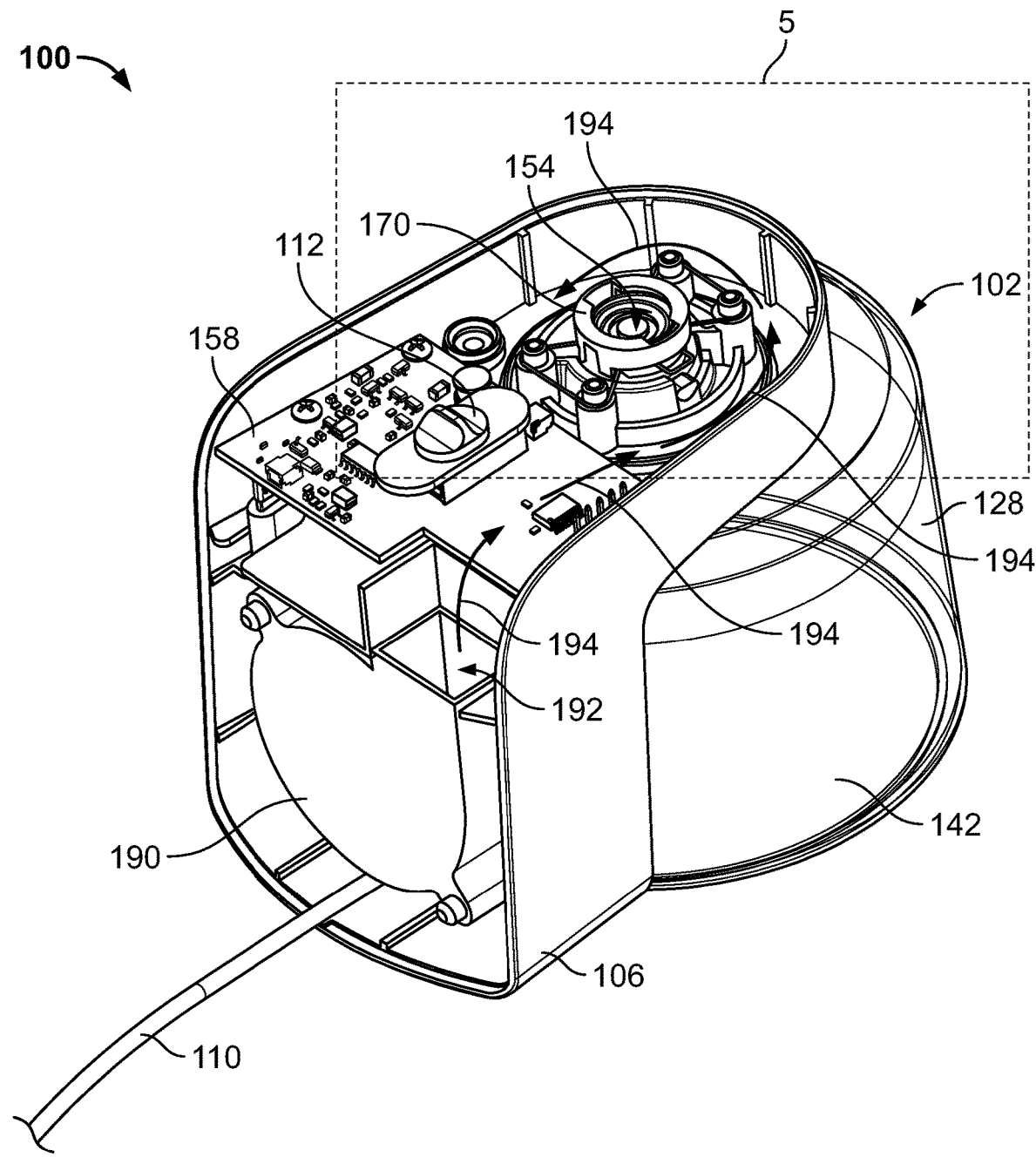
FIG. 5 is a top, rear, and left side perspective view of the device of FIG. 1 with an upper housing removed.

Referring to FIGS. 1 and 4, the atomizing device 100 includes a control switch 112 for adjusting a setting of the atomizing device 100. While a single switch is shown, any number of switches that adjust any number of different characteristics of the device 100 may be implemented. The top cover 108 also defines a fluid outlet 114 where volatile materials are dispensed into the environment surrounding the atomizing device 100. The top cover 108 further defines a plurality of air inlets 116 positioned on a lower portion 118 of the top cover 108. A plurality of air outlets 122 are defined by the top cover 108 in an upper portion 124. The plurality of air outlets 122 are positioned around the fluid outlet 114, the significance of the positioning of the plurality of air outlets 122 will be discussed later. As shown in FIG. 3, an edge of each of the plurality of air outlets 122 extends along an air plane 122a, which is defined by an upper surface 124a of the upper portion 124. Further, an edge of the fluid outlet 114 defines a fluid plane 114a that is parallel to the air plane 122a. Correspondingly, the plurality of air outlets 122 each extends along a respective central air axis 122b, and the fluid outlet 114 extends along a central fluid axis 114b, the central air axes 122b and the fluid axis 114b extending in a uniform direction. In the embodiment illustrated in FIG. 3, the air axes 122b and the fluid axis 114b are parallel.

Figure 2:
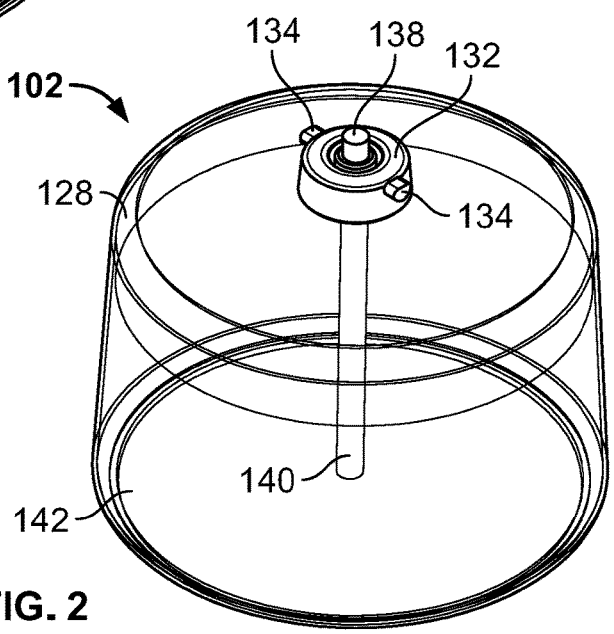
FIG. 2 is a top and front perspective view of a fluid reservoir for use with the device of FIG. 1.

Turning now to FIG. 2, the fluid reservoir 102 comprises a container 128 with a neck 130 (seen in FIG. 3). A combination plug and wick holder 132 is affixed to the neck 130, wherein the plug and wick holder 132 includes a pair of laterally extending mounting lugs 134. A wick 136 is disposed within the reservoir 102 in contact with fluid therein. An upper end 138 of the wick 136 extends beyond the neck 130 and a lower end 140 of the wick 136 is disposed within the fluid reservoir 102 toward a bottom surface 142 thereof. The wick 136 transfers liquid by capillary action from within the reservoir 102 to the upper end 138 of the wick 136. The base 106 of the device 100 defines a receiving aperture 144 (see FIG. 3) that includes opposed bayonet slots 146 (see FIG. 6). The fluid reservoir 102 is inserted into the base 106 by aligning the lugs 134 with opposed bayonet slots 146 and pushing the reservoir 102 upwardly, thereby inserting the lugs 134 into the respective bayonet slots 146 such that the plug and wick holder 132 is positioned within the housing 104 by passing through the receiving aperture 144. The fluid reservoir 102 is thereafter rotated to force the lugs 134 to engage with the walls 148 defining detent portions of the respective bayonet slots 146 to secure the fluid reservoir 102 within the atomization device 100. While a particular manner for attaching the fluid reservoir 102 to the device is described, the fluid reservoir 102 may be attached to the device in any suitable manner.

It is also contemplated that different methods may be employed by the interaction of the reservoir 102 and the base 106 to ensure that the correct materials and/or fluid reservoirs are being used with the device 100. In some embodiments, a sensor 150 (see FIG. 6) for identifying the reservoir 102 and/or compositions of fluids and/or fragrances in the reservoir 102 may be placed adjacent the receiving aperture 144. The sensor 150 may include electromechanical means that may be triggered by insertion of the reservoir 102 into the atomizing device 100. It is also contemplated that the electromechanical means may be placed in any convenient location on the base 106 so as to interact with the reservoir 102. For example, the lugs 134 or the plug and wick holder 132 may be shaped uniquely so as to trip a switch positioned above a portion of the receiving aperture 144. Other configurations are also contemplated. In other embodiments, the reservoir 102 may include a near field communication device (e.g., an RFID tag or an NFC chip) and the device 100 may include a complementary near field communication device (e.g., an RFID tag reader or an NFC chip reader) configured to read information stored on the near field communication device of the reservoir 102. Other types of sensors 150 may include Infra-red sensors and or other optical sensors that interact with printed information (e.g., one dimensional barcodes such as, UPC, EAN, CODE 39, CODE 128, ITF, CODE 93, CODEBAR, GS1 DATABAR, and MSI PLEASSEY, or two dimensional barcodes such as QR CODE, DATAMATRIX CODE, PDF147, and AZTEC) on the reservoir 102. It is also contemplated and will be discussed below that the sensor 150 may be used beyond just identification of authorized materials and reservoirs 102. For example, control functions based off of information transferred via the sensor 150 may also be included in the device 100. Any of the sensors or methods disclosed in Leonard et al. U.S. Pat. No. 7,009,519, owned by the assignee of the present application, may additionally or alternatively be used with the devices or methods disclosed herein.

Figure 6:
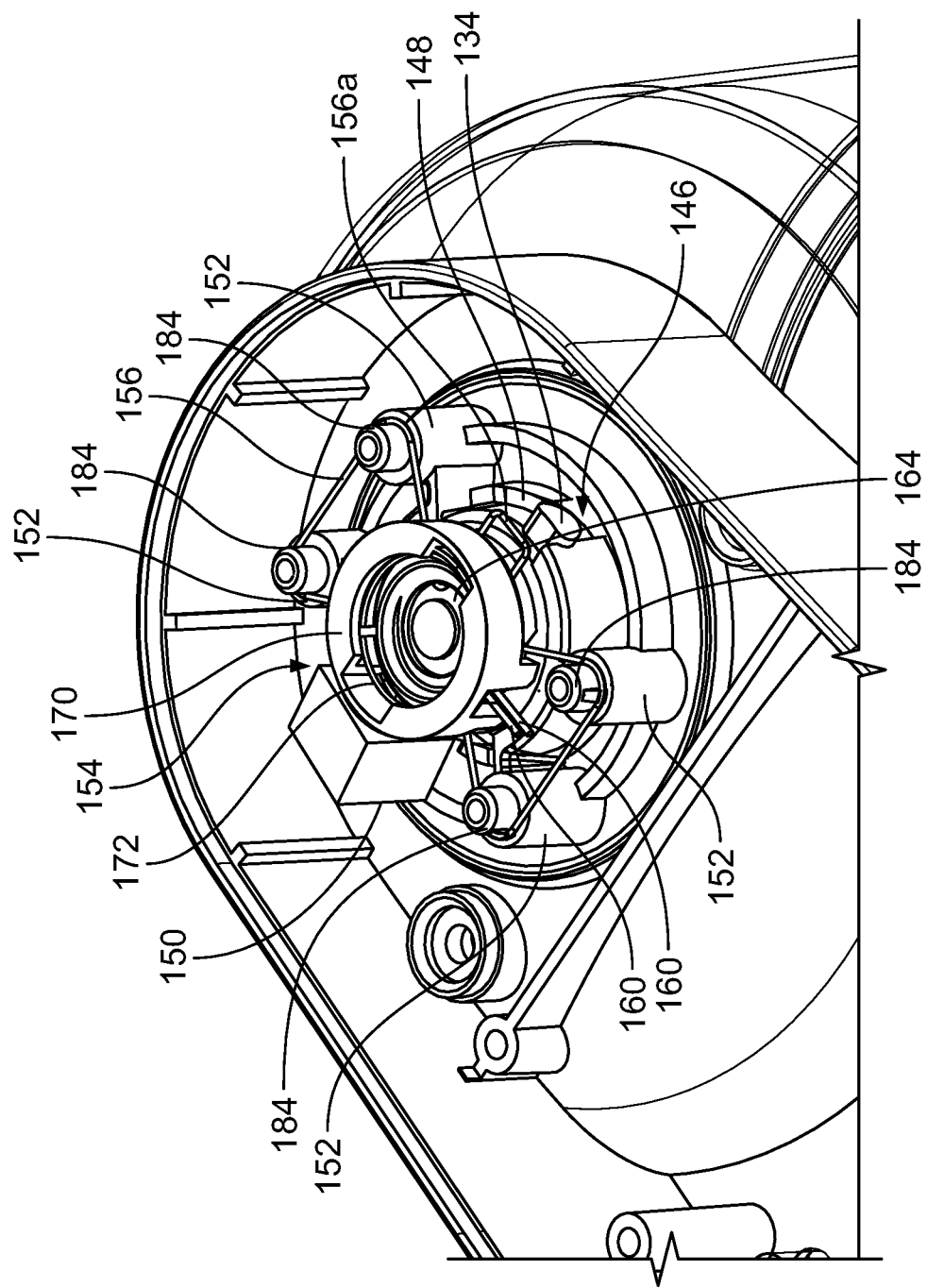
FIG. 6 is a detailed view of the region 5 in FIG. 5.
Figure 7:
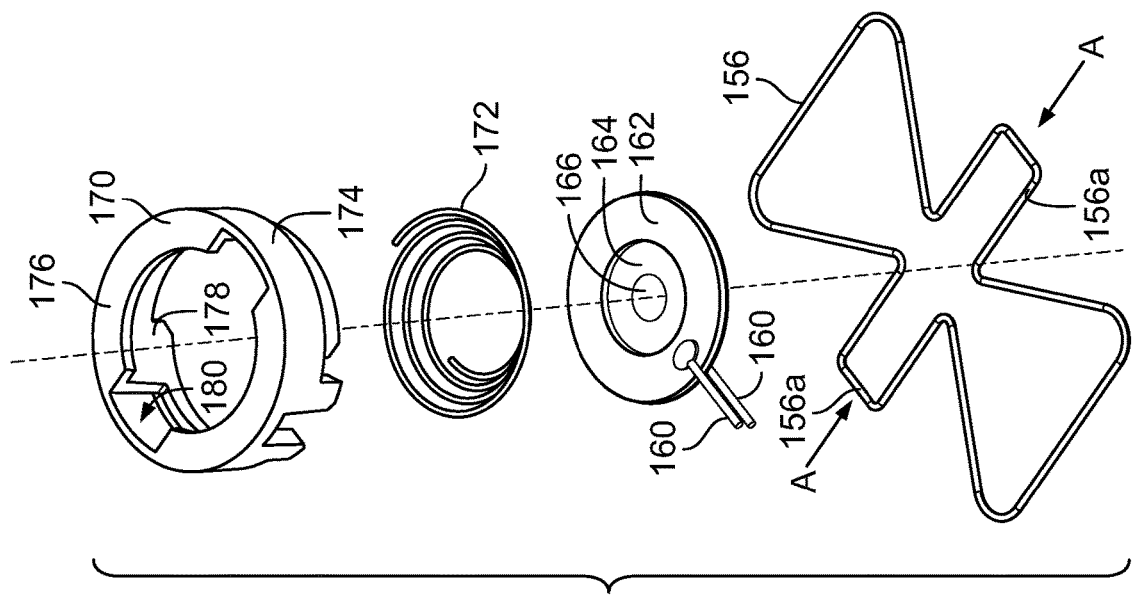
FIG. 7 is an exploded perspective view of an atomizing assembly used in the device of FIG. 1.
Figure 7:
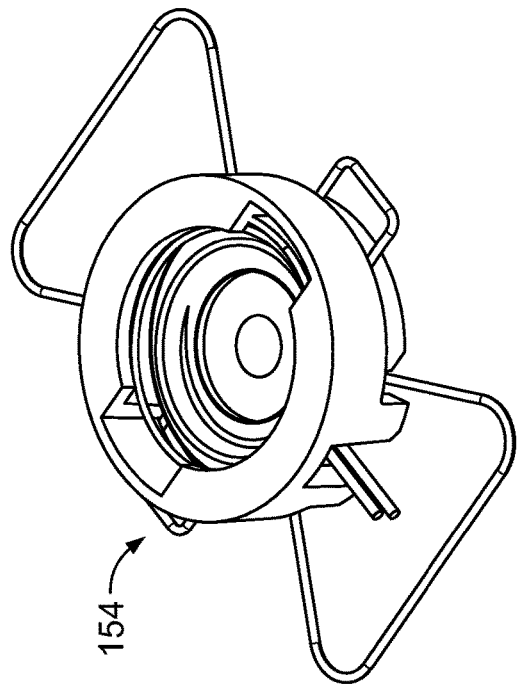
Figure 8:
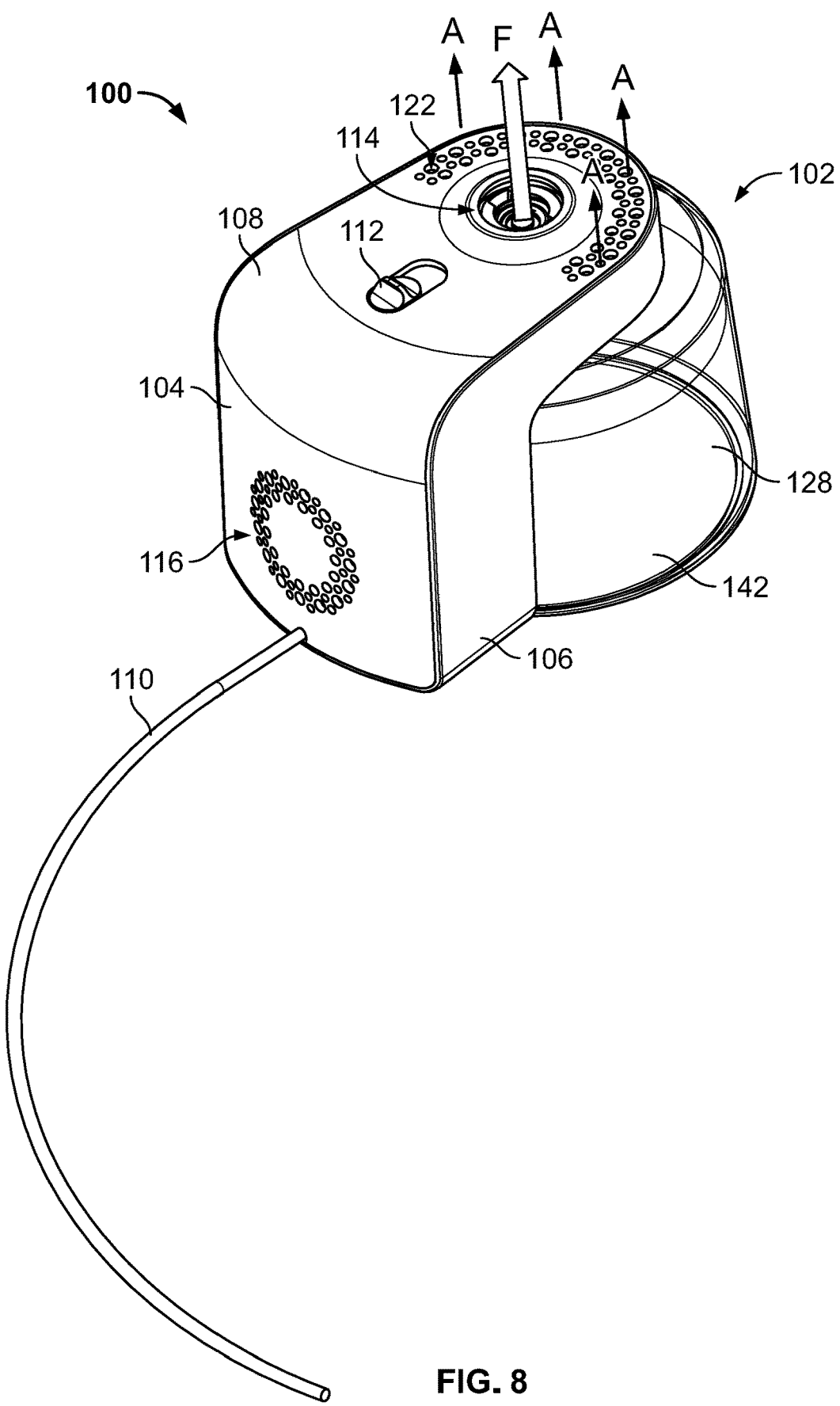
FIG. 8 is a top, rear, and left side perspective view of the device of FIG. 1 depicting the external air flow and active emitting characteristics of the device of FIG. 1.
Figure 9:
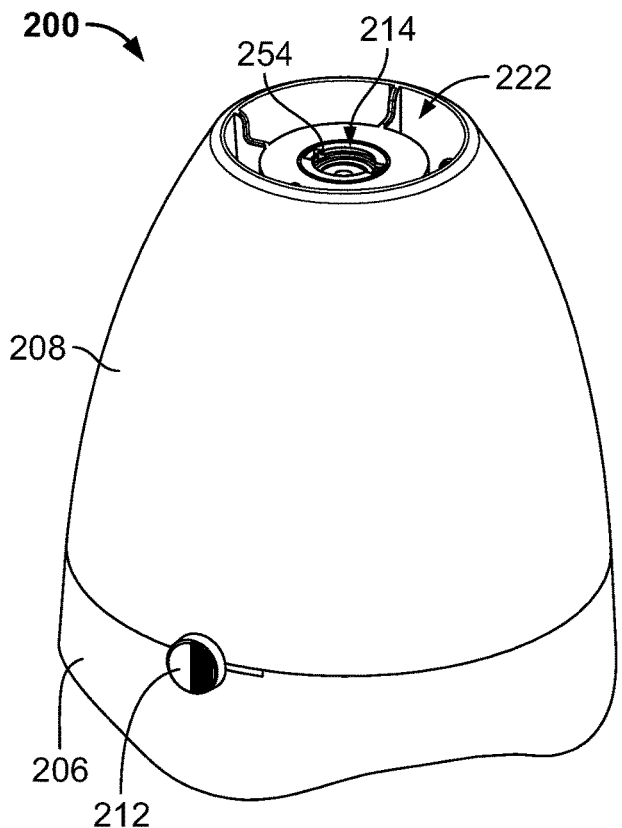
FIG. 9 is a top, front, and right side perspective view of a second embodiment of an exemplary piezoelectric active emitting device that may embody the principles of the present disclosure.
Figure 14:
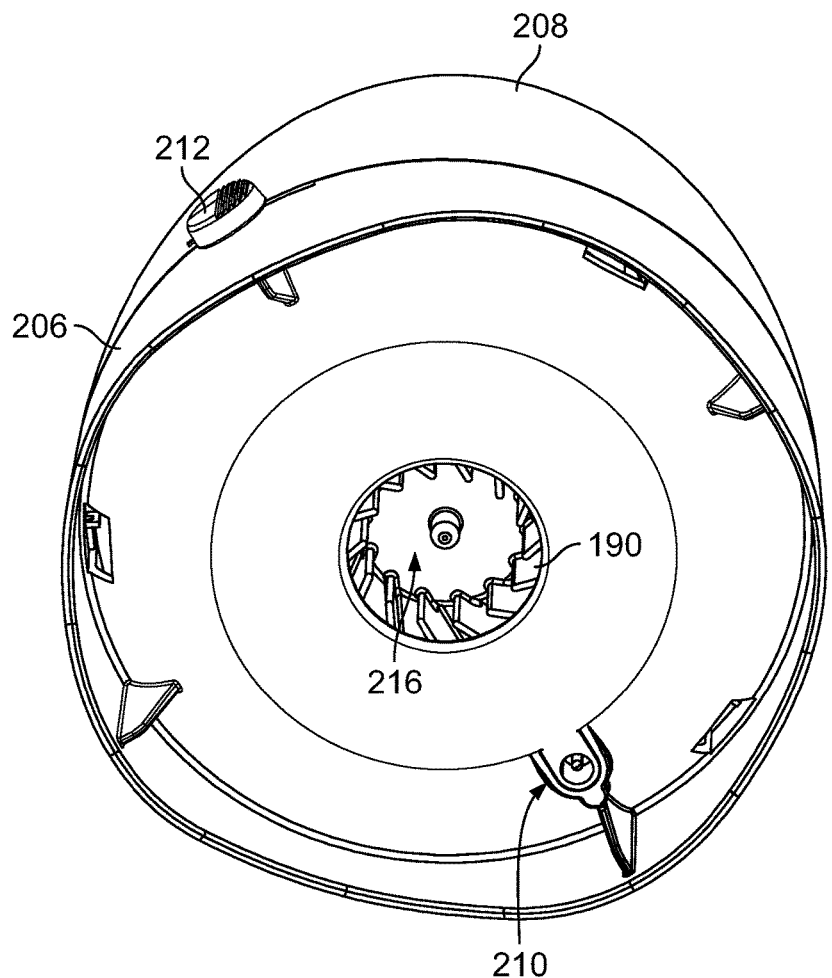
FIG. 14 is a bottom perspective view of the device of FIG. 9.
Figure 15:
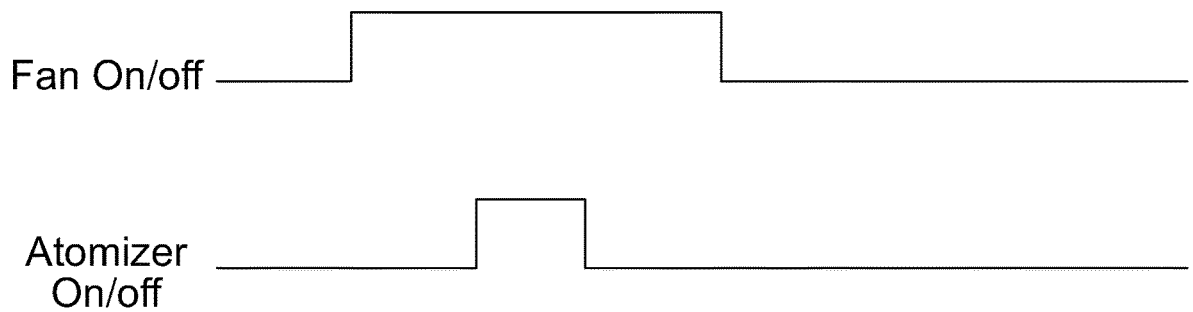
FIG. 15 is diagram depicting an exemplary control algorithm that may be utilized with any of the exemplary piezoelectric active emitting devices of the present disclosure.

As shown in FIG. 6, a plurality of mounting posts 152 extend upwardly from the base 106 and are distributed around the receiving aperture 144. An atomizing assembly 154 is mounted on the chassis above the receiving aperture 144 by means of a support wire 156 which is looped about and extends from the mounting posts 152 to the atomizing assembly 154. A printed circuit board 158 is mounted on the base 106 (see FIG. 5). This printed circuit board 158 is provided with electrical circuits which are connected to be powered by electrical connection 110 and which are configured to produce energization voltages for the atomizing assembly 154. These voltages are communicated via electrical lines 160 to a ring-shaped piezoelectric actuator 162 (see FIG. 7) in the atomizing assembly 154 where they impose alternating electrical fields across the thickness of the actuator and cause it to expand and contract in radial directions. An orifice plate 164, which is formed in a center region thereof with minute orifices, is secured to and extends across a center opening in the actuator 162. The radial expansion and contraction of the piezoelectric actuator 162 causes it to push the center region of the orifice plate 166 up and down in a vibratory manner. During this vibratory movement liquid from the container 128 is delivered by a capillary element or wick 136 up to the underside of the orifice plate 164. The up and down movement of the plate drives the liquid through its orifices so that the liquid becomes separated into small liquid droplets which are then ejected in the form of a mist out through the fluid outlet 114 in the top cover 108.

It is contemplated that the sizes of the orifices in the orifice plate 154 may be optimized for different types of fragrance compositions or other volatile compositions dependent upon the base materials. For example, water based versus oil based compositions have different requirements to produce particles that are above inhalation requirements. Furthermore, the cost of producing an orifice plate 154 is reduced as the orifices are increased in size. As will be discussed later, a device that produces a separate flow of air allows for larger orifices that produce larger droplets. This allows for producing a device with improved economics while matching or exceeding the performance of the prior art devices.

The construction of the atomizing assembly 154 is shown in the exploded view of FIG. 7. This assembly includes a retainer 170, a coil compression spring 172, the piezoelectric actuator 162, and the orifice plate 164. The retainer 170 may be made of plastic and may have a hollow cylindrical body 174. An upper rim 176 extends inwardly at the upper end of the body 174 and a pair of lower flanges 178 extend downwardly from its lower end. Each of the flanges 178 is formed with an elongated circumferentially extending slot 180. In assembling the atomizing assembly 154, the coil compression spring 172 is inserted into the bottom of the retainer 170 and pushed up against its upper rim 176. The piezoelectric actuator 162 with the orifice plate 164 soldered thereto is then pushed up against the spring 172 until the actuator 162 is located above the slots 180. Then the support wire 156 is squeezed inwardly in the direction of the arrows A, A so that projections **156*a* thereon can fit between the lower flanges 178. The projections 156*a* are aligned with the slots 180 and allowed to spring back to their normal configuration upon release of the squeezing force on the wire 156. This allows the projections 156*a* to become inserted into the slots 180 where they are held by the resilient characteristics of the support wire 156. Further, the portions of the wire support 156 adjacent the projections 156*a* extend into the retainer 40 and support the piezoelectric actuator 162 and the orifice plate 164 against the force of the coil spring 172**.

The support wire 156, with the atomizing assembly 154 thus secured thereto, is then mounted on the atomizer device by looping the support wire over upper cylindrical portions 184 of the mounting posts 152, respectively, as shown in FIG. 2. The support wire 156 is held in place by detents 186 formed in the upper cylindrical portions of the mounting posts. While the atomizing assembly 154 is disclosed herein as having a specific configuration and specific components, any other suitable configuration and/or components may be utilized.

Turning now to FIGS. 3-5 and 8, the atomizing device includes a fan assembly 190 (see FIGS. 3 and 5) which is configured to draw air into the housing 104 through the plurality of air inlets 116 and push air out of the fan assembly outlet 192. The base 106 and the top cover 108 define an air channel 194 (see arrows depicted in 5) from the fan assembly outlet 192 through the housing 104 and around the atomizing assembly 154. The top cover 108 includes walls (not shown) that interact with the base 106 to isolate the atomizing assembly 154 and contain all of the air flow within the housing 104 to the air channel 194. The air within the air channel 194 is forced out of the plurality of air outlets 122 positioned around the fluid outlet 114. In this manner, the air flow does not interact with the volatile materials until after the air flow has exited the air outlets 122.

Turning now to FIG. 8, the air flow characteristics and some advantages of the atomizing device 100 will be discussed. The mist of fluid that is ejected from the fluid outlet 114 is depicted by the arrow F. The air flow out of the plurality of air outlets 122 is depicted by the arrows A. It can be seen in FIG. 8 that the air flow out of the outlets 122 forms a partial column of air around the mist of fluid F. This configuration is one way to overcome the problem of fallout on and around the atomizing device 100. The fan assembly is capable of moving air between the inlets 116 and the outlets 122 at the rate between at least 4 cubic feet per minute (4 CFM) and 8 or more cubic feet per minute (8 CFM). One having skill in the art would understand the fan configuration, centrifugal and others, that are capable of performing the required air flow. In order to prevent fallout, the atomizing assembly 100 is operated according to the control algorithm depicted in FIG. 15. First, the fan assembly 190 is activated and the atomizing assembly 154 is not activated. In some embodiments, the air flow A is greater than or equal to at least 4 cubic feet per minute. This level of air flow A creates air currents in the environment around the atomizing device 100. A period of time after the activation of the fan assembly 190, the atomizing assembly 154 is activated, creating the mist of fluid F. By having the air flow at or above 4 CFM, the droplets in the mist F are carried away from the atomizing device 100 far enough that fallout onto or around the atomizing device 100 is minimized or prevented. It has been shown in testing that the column of air above the atomizing device 100 containing the mist F reaches proximate the ceiling in most residential structures when 4 CFM or more air flow. This significantly reduces the chance of a droplet landing near or on the atomizing device 100. The atomizing assembly 154 is operated for a short duration and then deactivated while the fan assembly 190 remains operating to ensure the last of the mist F is carried away.

It is contemplated that the timing of the operation of the atomizing assembly 154 may be controlled by a user to adjust the amount of the active material in the environment. The control switch 112 may be a slider switch that moves between a maximum setting and a minimum setting for the activation time of the atomizing assembly 154. In one exemplary embodiment, each activation time is between 2 and 5 seconds (for example, the slider switch may have a maximum setting at 5 seconds, an intermediate setting at 3.5 seconds, and a minimum setting at 2 seconds). In another embodiment, each activation time of the atomizing assembly may be between 2 and 10 seconds (for example, the slider switch may have a maximum setting at 10 seconds, an intermediate setting at 6 seconds, and a minimum setting at 2 seconds). The time the fan assembly 190 is operational before and after the atomizing assembly 154 may be a constant value or may vary with the activation time of the atomizing assembly 154. In one exemplary embodiment, the time the fan assembly 190 is activated may be between 0 seconds and 60 seconds before the activation of the atomizing assembly 154, or between 10 seconds and 50 seconds. It is contemplated that the operational time of the fan assembly after the atomizing assembly 154 is deactivated may be the same of different in some embodiments. Further, it is contemplated that the atomizing device 100 may have a control function that operates the control algorithm as described above on a regular time interval. The time interval may be varied to control the amount of active material dispensed into the environment around the atomizing device 100.

It is also contemplated that in some embodiments the control switch 112 may activate a programmable controller that provides different operating responses of the device 100 based on information received via the sensor discussed above. First, the device 100 may not operate if there is no information from the sensor. For example, an unauthorized reservoir that contains an unknown composition will not properly trigger the sensor or provide the proper information to allow the device 100 to operate. Further, the information provided via the sensor may include operational information pertaining to the specific fragrance composition. For example, the timing of the activation of the device 100 and/or other parameters of the device 100 operation may be adjusted. Some operating parameters may include on/off cycle timing for fragrance release, increasing or decreasing the release rate of the fragrance composition, time of day for operation, and/or season of the year. Further, in some embodiments the programmable controller may include a plurality of pre-programmed algorithms that are selected by the programmable controller based on the fragrance composition and/or user inputs.

It is also contemplated that in some embodiments the device 100 may be a smart device that utilizes Internet of Things (IoT) types of technology to allow the device 100 to interact with a user locally or via a remote connection. For example, the device may communicate by various means including wireless technologies such as WIFI or Bluetooth to interact with an application on a user's smartphone or other device. Further, the device 100 may include technology and/or programing to interact via Apple® Homekit™, Amazon® Alexa™, or Google® Home systems. For example, it is contemplated that a user's phone or other device might be recognized via various wireless of location technologies associated with the aforementioned systems and when the user comes home the device would begin an activation cycle of dispensing a fragrance composition based upon pre-selected conditions or deactivate upon detection that the user has departed the premises. Further, in some embodiments the user may be able to interact with the device remotely through an application on the user's smartphone or other device so that the user can control the device 100 via the aforementioned systems or other communications types and/or systems available for remote communication and operation.

Now turning to FIGS. 9-14, a second exemplary embodiment of an atomizing device 200. The characteristics and elements atomizing device 200 that are shared with the atomizing device 100 are labeled with the same numerical designator plus 100. The atomizing device 200 includes a housing 204 that comprises a base 206 and a top cover 208. The electrical connection 210 is depicted as a receptacle in FIG. 14. It is contemplated that many types of cables could connect to the atomizing device 200 to provide electrical power from a variety of sources. The top cover includes a fluid outlet 214. The fluid outlet 214 is surrounded by a plurality of air outlets 222. Air enters the atomizing device 200 through a single air inlet 216 defined by the base 106 (see FIG. 14).

Figure 12:
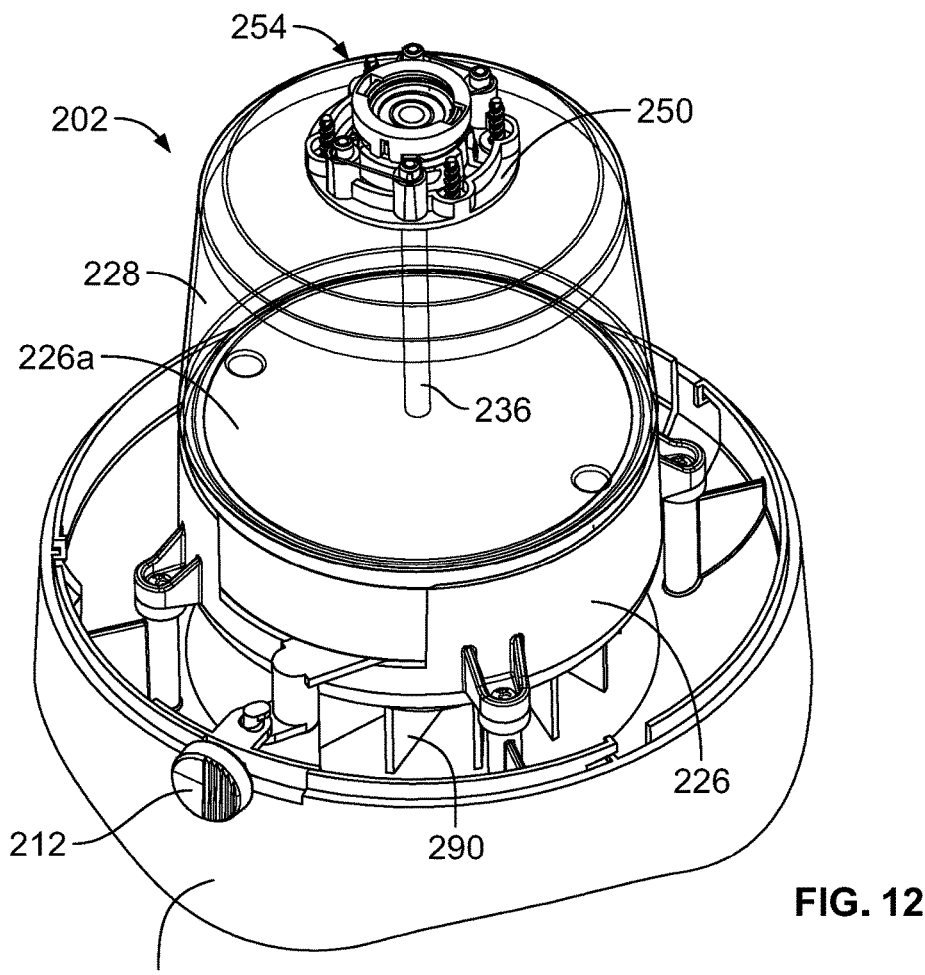
FIG. 12 is a top, front, and right side perspective view of the device of FIG. 9 with an upper housing portion removed.
Figure 13:
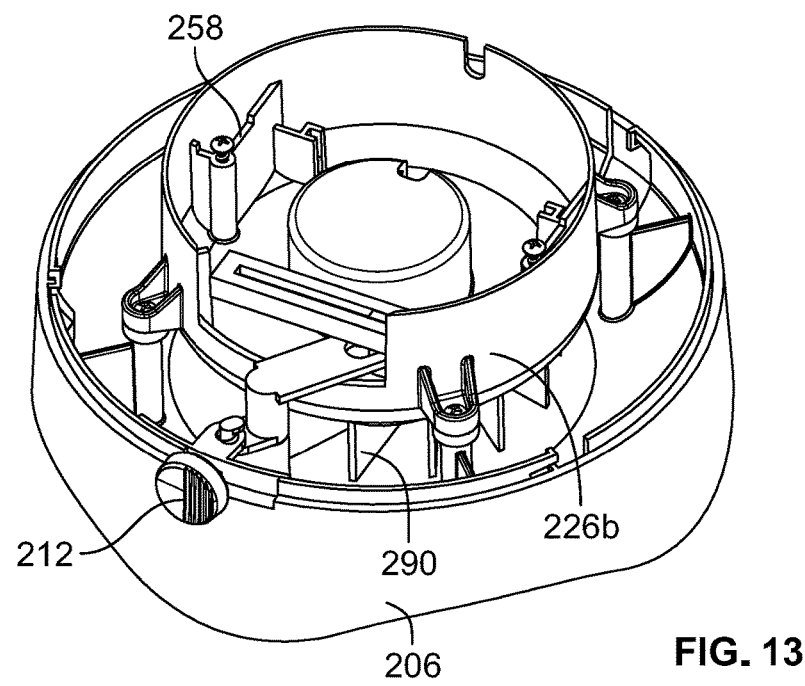
FIG. 13 a top, front, and right side perspective view of a lower and intermediate housing of the device of FIG. 9.

Turning to FIG. 12, a fluid reservoir 202 is identical to the fluid reservoir 102. The fluid reservoir connects to the housing in a similar fashion as the first embodiment, except that the receiving aperture 244 and opposed bayonet slots 246 are formed in a mounting housing 250, which in turn is coupled to the underside of a central portion 220 of the top cover 208 that surrounds the fluid outlet 214 and separates the fluid outlet 214 from the plurality of air outlets 222. The atomizing device 200 includes an atomizing assembly 254 that is identical to the atomizing assembly 154 and retained in position above the fluid reservoir 202 on the mounting housing 250 in the same manner. The mounting housing 250 includes the same structural elements as the base 106 to support and retain the atomizing assembly 254. The fan assembly 290 is positioned above the air inlet 216 and below a middle housing 226. The middle housing 226 includes an upper portion 226a that supports the fluid reservoir 202 and a lower portion 226b that defines a volume where the printed circuit board 258 (shown as a transparent structure to reveal the linkage with a control switch 212). The control switch 212 extends through the housing 204 to give users control over the atomizing device 200 in a similar fashion as the atomizing device 100.

Figure 10:
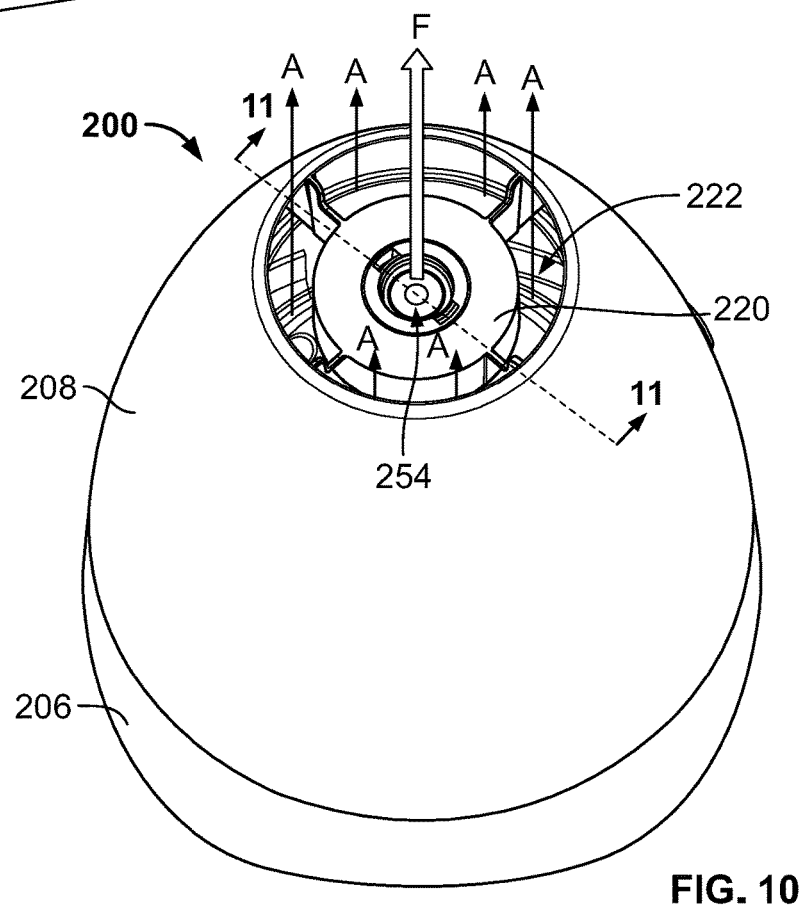
FIG. 10 is a top, rear, and left side perspective view of the device of FIG. 9.
Figure 11:
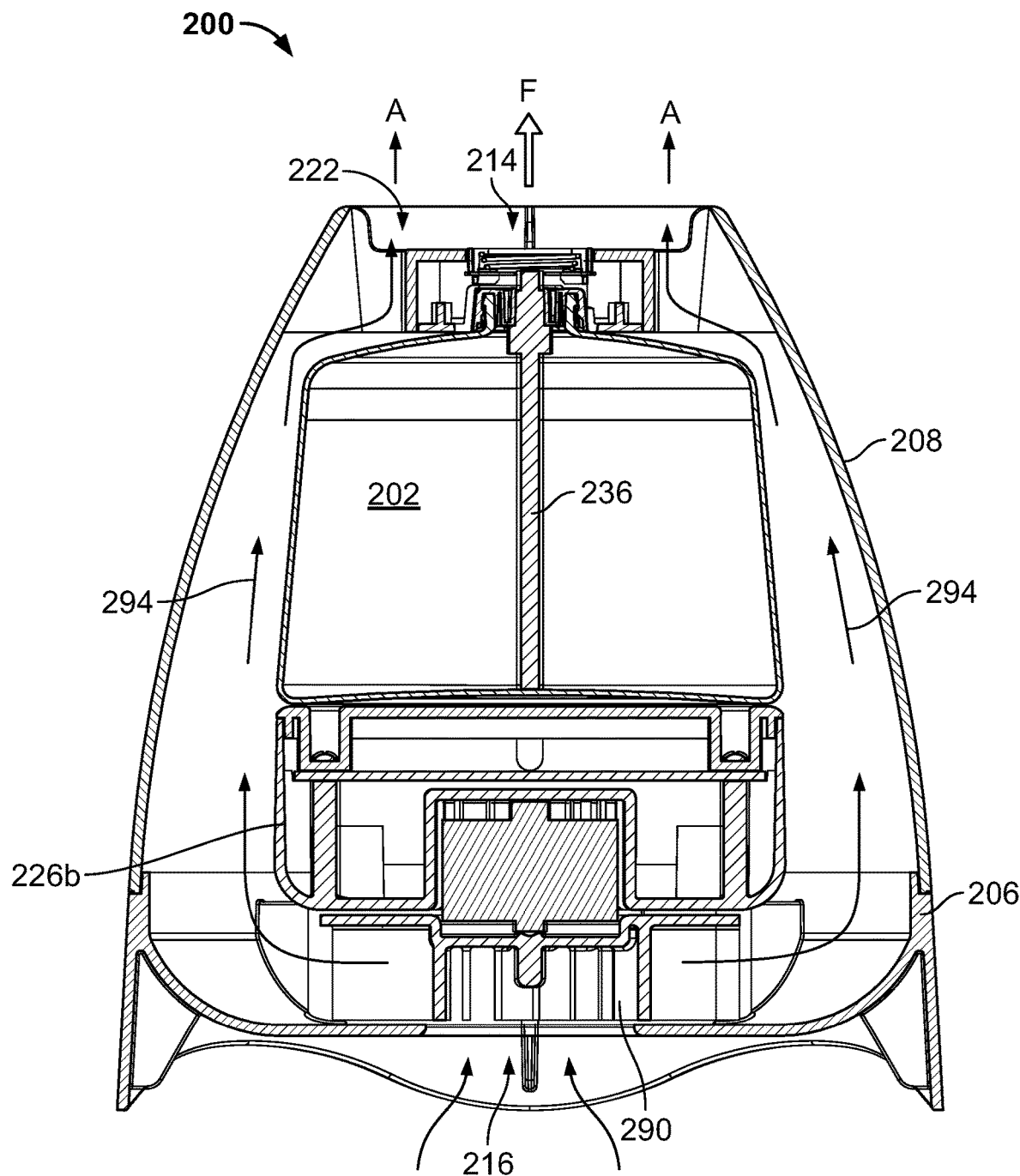
FIG. 11 is a cross-sectional view of the device of FIG. 9 generally taken along the lines 11-11 of FIG. 10.

Turning to FIGS. 10 and 11, the air flow characteristics of the atomizing device 200 are similar to the atomizing device 100. The air channel 294 is depicted by arrows in FIG. 11. The air is sucked into through the inlet 216 in the base 206. The fan assembly 290 pushes the air out around the fluid reservoir 202 and up the inside of the top cover 208 until it exits out of the plurality of outlets 222. The air flow A out of the outlets 222 forms the same exterior air column around the mist F exiting the atomizing assembly 254. It is contemplated that the atomizing device 200 may be operated with the same methodology and algorithms as the atomizing device 100.

Turning now to FIGS. 16-22, alternative embodiments that utilize modified structures and air flows to achieve similar fluid mist dispersion results and prevent volatile material fallout on and around the disclosed devices are discussed. Specifically in FIGS. 16 and 17, an atomizing device 300 includes a base 302 defining a plurality of air inlets 304. A top cover 306 defines a main air and fluid outlet 308 and is coupled to the base 302 by a cylindrical midsection 310. A fan assembly 312 is positioned within the base 302 and configured to draw air in through the plurality of air inlets 304. The mid-section 310 and the top cover 306 define an interior volume 314 of the atomizing device 300. A fluid reservoir 316 includes a wick 318, wherein an end of the wick 318 is in fluid communication with an atomizing assembly 320. An inner nozzle assembly 322 defines an inner fluid outlet 324. The fluid reservoir 316, inner nozzle assembly 322 and the atomizing assembly 320 are all positioned within the interior volume 314 of the atomizing device 300. The inner nozzle assembly 322 is positioned over an upper end of the fluid reservoir 316. The atomizing assembly 320 is positioned within the inner nozzle assembly 322 slightly below the inner fluid outlet 324. A honeycomb array 326 may be positioned around the exterior of a lower portion of the inner nozzle assembly 322 within the interior volume 314.

Figure 16:
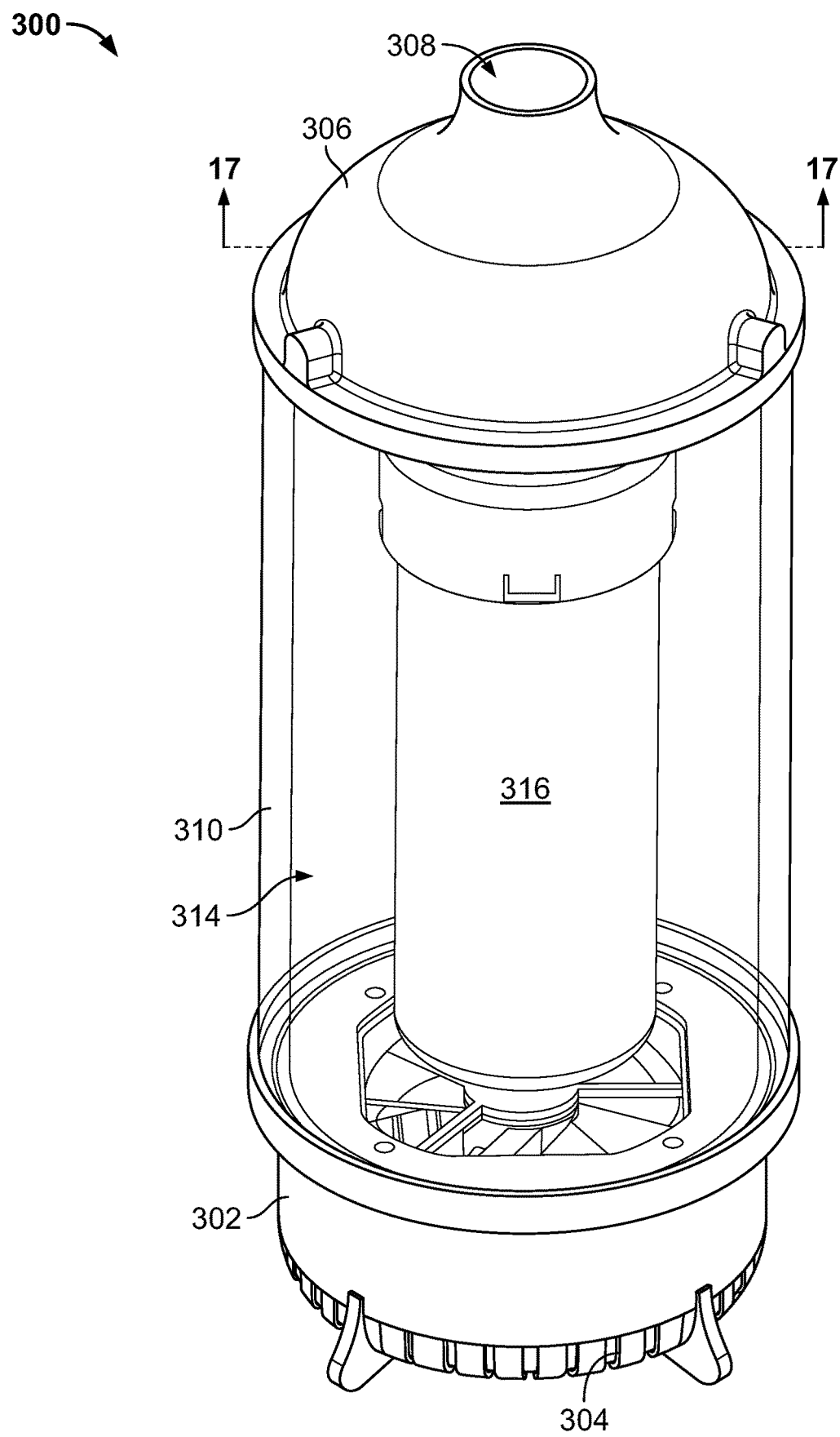
FIG. 16 is a top and front perspective view of a third embodiment of an exemplary piezoelectric active emitting device that may embody the principles of the present disclosure.
Figure 17:
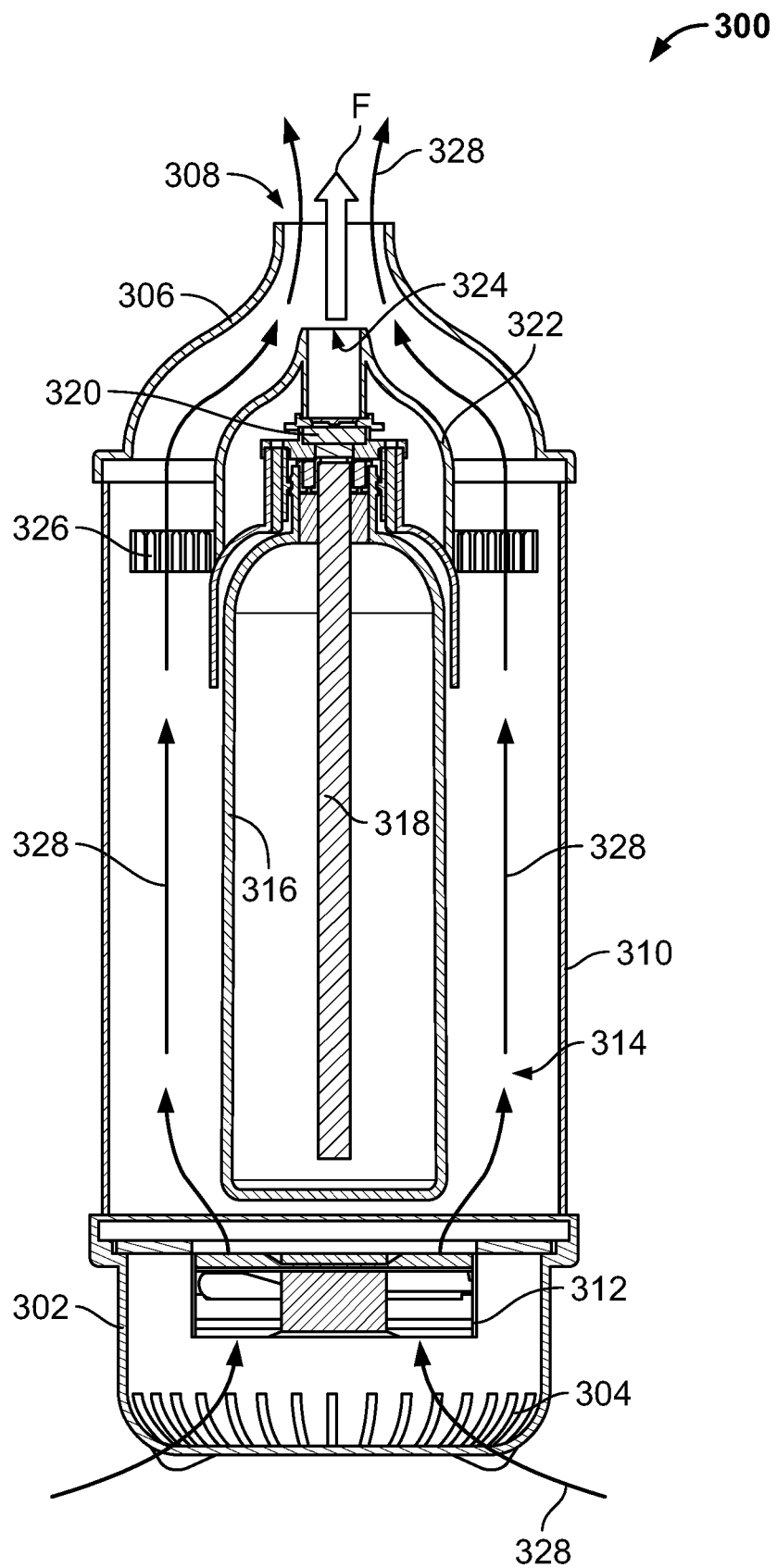
FIG. 17 is a cross-sectional view of the device of FIG. 16 generally taken along the lines 17-17 of FIG. 16.

Continuing to refer to FIGS. 16 and 17, the fluid reservoir 316, the wick 318, and the atomizing assembly 320 all function is the same manner as disclosed above to produce a mist of fluid particles F that is ejected out of the inner fluid outlet 324. The fan assembly 312 creates an airflow 328 that passes though the honeycomb array 326 (to reduce swirling of the airflow 328) and passes through the interior volume 314 between the top cover 306 and the inner nozzle assembly 322. The mist of fluid F and the airflow 328 exit the main air and fluid outlet 308 in the form of a laminar jet projecting the mist of fluid F high above the atomizing device 300. Testing has shown with air flow rates above 4 CFM that a significant quantity of the fluid particles within the air flow 328 reach over 4 feet above the atomizing device 300 and disperse into the environment, significantly preventing and/or reducing fallout on/around the atomizing device 300.

Figure 18:
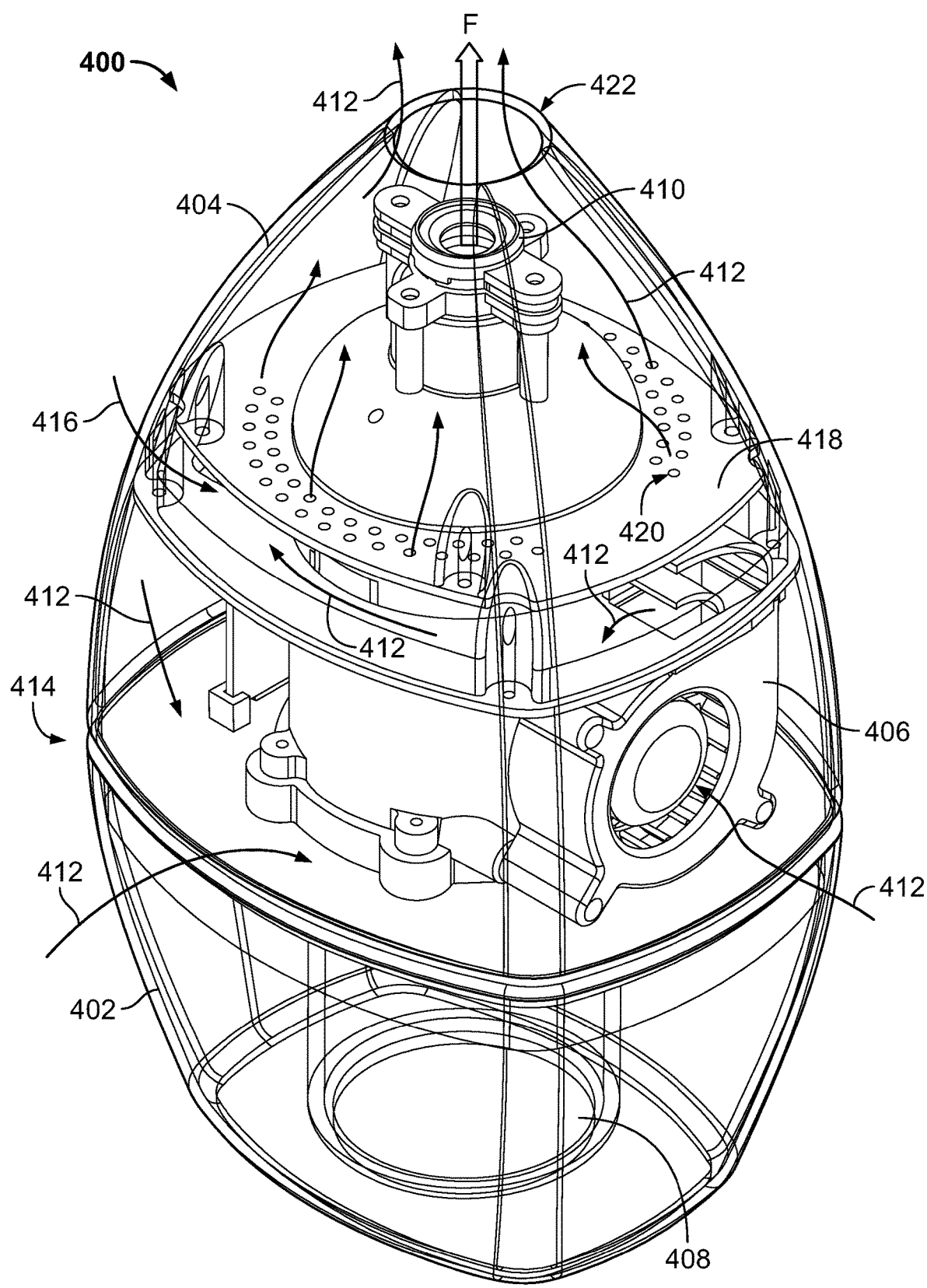
FIG. 18 is a top, front, and right side perspective view of a fourth embodiment of an exemplary piezoelectric active emitting device that may embody the principles of the present disclosure.

Referring now to FIG. 18, another embodiment of an atomizing device 400 is depicted. The atomizing device 400 operates similarly to the embodiments previously disclosed and includes a base 402, a top cover 404, a fan assembly 406, a fluid reservoir 408, and an atomizing assembly 410. A fluid mist F is produced as discussed above. The airflow 412 of the atomizing device 400 begins with air drawn in through a gap 414 between the base 402 and the top cover 404. The airflow 412 passes through the fan assembly 406 and into a pre-mixing volume 416 below an anti-swirl plate 418. The airflow 412 passes through apertures 420 defined by the anti-swirl plate 418 and up past the atomizing assembly 410 before exiting through a main air and fluid outlet 422. Generally, the atomizing device 400 operates the same as the atomizing device 300 with a slightly different form-factor and airflow path.

Figure 19:
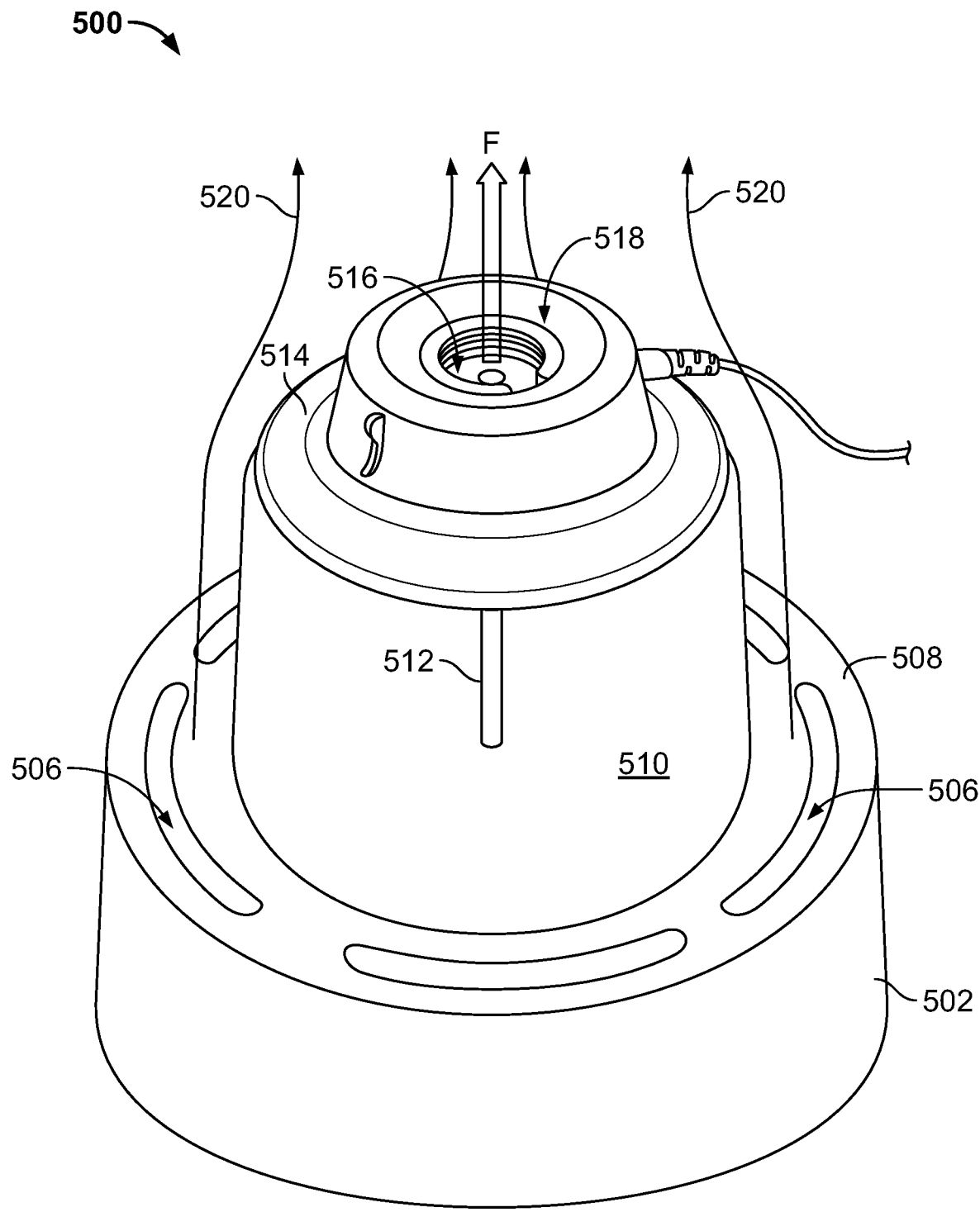
FIG. 19 is top and front perspective view of a fifth embodiment of an exemplary piezoelectric active emitting device that may embody the principles of the present disclosure.
Figure 20:
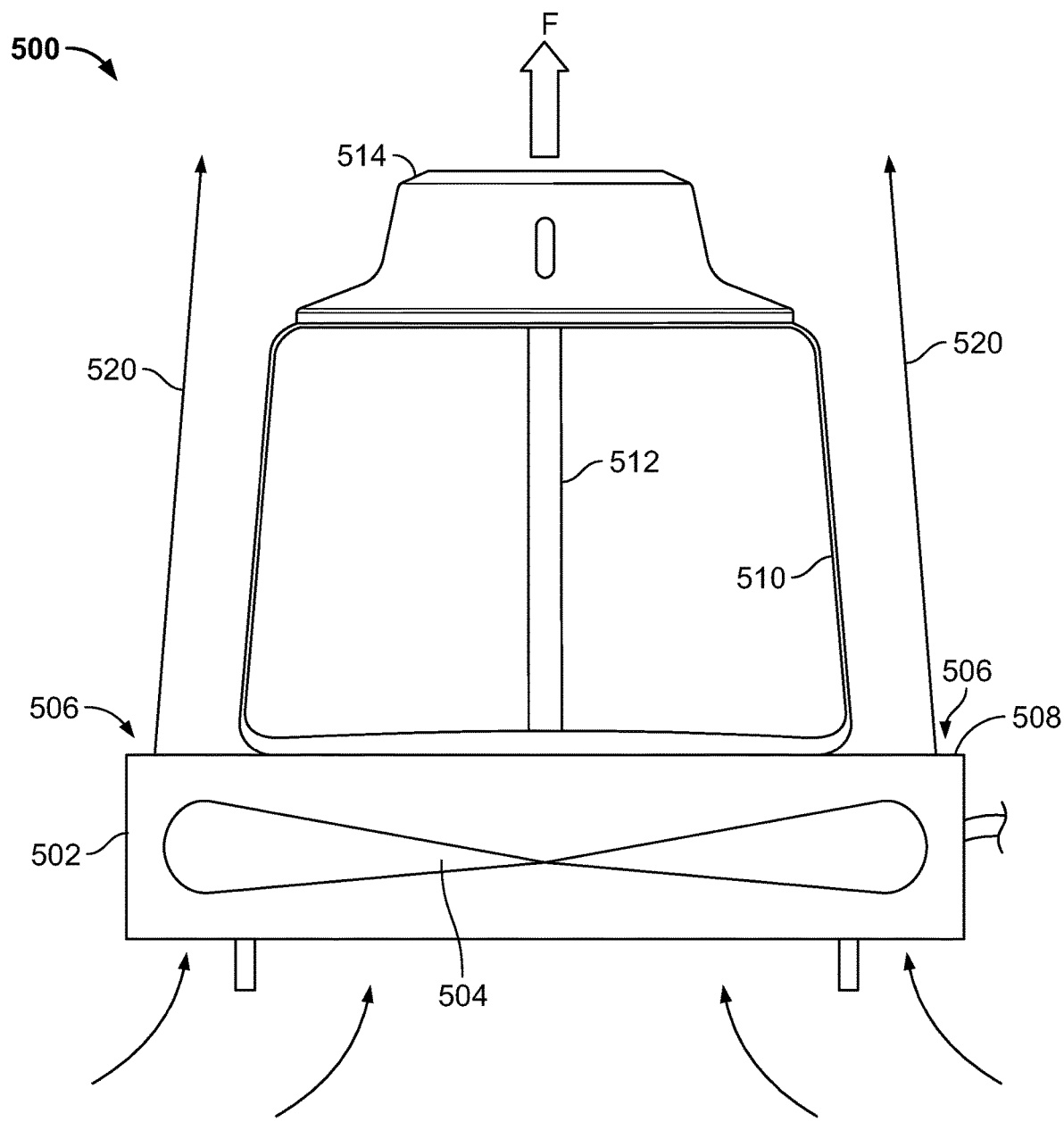
FIG. 20 is a front elevational view of the device of FIG. 19.

Turning now to FIGS. 19 and 20, another embodiment of an atomizing device 500 is depicted. A base unit 502 includes a fan assembly 504 positioned within the base unit 502 and a plurality of outlets 506 are defined in a top surface 508. A fluid reservoir 510 including a wick 512 and is supported by or detachably attached to the top surface 508 of the base unit 502. A top unit 514 is positioned on an upper portion of the fluid reservoir 510. The top unit 514 includes an atomizing assembly 516 that operates as disclosed above to produce a fluid mist F that is dispensed from a fluid outlet 518 formed in the top unit 514 above the atomizing assembly 516. An airflow 520 created by the fan assembly 504 exits the plurality of outlets 506 around a perimeter of the top surface 508 and flows up past the top unit 514. Generally, the atomizing device 500 operates with the air flow 520 carrying the fluid mist F up and away from the atomizing device to prevent and/or reduce the fallout of any materials from the fluid mist onto or around the atomizing device 500.

Turning now to FIG. 21, an atomizing device 600 similar to the atomizing device 500 is disclosed. A base 602 includes a fan assembly 604. A fluid reservoir 606 is positioned on a top surface 608 of the base 602. A top unit 610 is positioned on an upper end of the fluid reservoir 606. The top unit 610 includes an atomizing assembly 612 that operates with the fluid reservoir 606 to produce a mist of fluid particles F as described above. An airflow 614 is provided between the fan assembly 604 in the base 602 to the top unit 610 by a tube 616. The atomizing devices 500, 600 include the advantage of easily replacing the fluid reservoirs 510, 606 by removing the top units 514, 610 when all of the fluid is consumed and placing a full fluid reservoir 510, 606 on the base 502, 602. The top units 514, 610 may then be reattached to the full fluid reservoirs 510, 606 and the atomizing devices 500, 600 are ready to continue dispensing volatile materials.

Referring now to FIG. 22, an atomizing device 700, which is similar to the device 300 in FIGS. 16 and 17, includes a housing 702 having a fan 704 positioned in a lower portion of the housing 702 below a fluid reservoir 706. An atomizing assembly 708 is positioned on an upper end of the fluid reservoir 706 to produce a mist of fluid particles F. The housing includes a plurality of vents 710 formed in the central cylindrical portion 712 of the housing 702. Air is pulled into the housing 702 through an inlet 714 positioned below the fan 704. An airflow 716 flows from the fan 704 up past the fluid reservoir 706 and out a main outlet 718 along with the mist F. The air flow 716 past the vents 710 pulls in more air through the vents 710.

The active material disposed in the fluid reservoirs 102, 202, 316, 408, 510, 606, and 706 may be a volatile material comprising a water-based fragrance composition. In other embodiments, the volatile material may be selected from one or more of a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air freshener, a deodorizer, or any other suitable volatile material, and combinations thereof.

In illustrative embodiments, the water-based fragrance composition includes water, first and second organic solvents, and one or more fragrance formulations. In illustrative embodiments, the water-based fragrance composition may include at least about 70 wt % water, between about 5 and about 17 wt % of the first organic solvent, between about 0 and about 22 wt % of the second organic solvent, and about 5 wt % or less of the one or more fragrances. In illustrative embodiments, the components of the water-based fragrance composition may form a homogenous liquid phase.

Fragrances may be purchased from commercial vendors. Fragrances include one or more components. The components in fragrance may include one or more fragrance oils, surfactants, solvents, water, dyes, chlorophyll, stabilizers, emulsifiers, UV inhibitors, antioxidants, other additives, and/or any other suitable components. Fragrances, also called fragrance formulations herein, may have any of a wide variety of particular scents.

The first organic solvent is a component of the water-based fragrance composition that includes a relatively volatile, water soluble, low molecular weight organic compound or multiple such compounds. A compound is considered "water soluble" if a saturated solution of water includes at least 0.5 wt % of the compound. When calculating desirable ranges for the water-based fragrance composition, all of the relatively volatile, water soluble, low molecular weight organic compound or compounds present in the water-based fragrance composition are considered part of the first organic solvent. In illustrative embodiments, the first organic solvent may have a boiling point of less than about 100° C. Additionally, each of the relatively volatile, water soluble, low molecular weight organic compounds of the first organic solvent are defined as relatively volatile because each compound has a boiling point less than about 100° C. In illustrative embodiments, the first organic solvent may include one or more relatively volatile, water soluble, low molecular weight organic compounds selected from alcohols, ethers, ketones, esters, and the like, or combinations thereof.

In illustrative embodiments, the first organic solvent may or may not be volatile organic compounds (VOCs), as defined by California's Regulation for Consumer Products. As of this writing, an unofficial version of the Regulation for Consumer Products may be found at <http://www.arb-.ca.gpv/consprod/regs/2015/article_1_final_1-22-15.pdf>, definition (138). An official version may be found at <http://www oal.ca.gov/CCR.htm>. The Regulation for Consumer Products defines a VOC as follows:

"Volatile Organic Compound (VOC)" means any compound containing at least one atom of carbon, excluding carbon monoxide, carbon dioxide, carbonic acid, metallic carbides or carbonates, and ammonium carbonate, and excluding the following:

(A) methane,
methylene chloride (dichloromethane),
1,1,1-trichloroethane (methyl chloroform),
trichlorofluoromethane (CFC-11),
dichlorodifluoromethane (CFC-12),
1,1,2-trichloro-1,2,2-trifluoroethane (CFC-113),
1,2-dichloro-1,1,2,2-tetrafluoroethane (CFC-114),
chloropentafluoroethane (CFC-115),
chlorodifluoromethane (HCFC-22),
1,1,1-trifluoro-2,2-dichloroethane (HCFC-123),
1,1-dichloro-1-fluoroethane (HCFC-141b),
1-chloro-1,1-difluoroethane (HCFC-142b),
2-chloro-1,1,1,2-tetrafluoroethane (HCFC-124),
trifluoromethane (HFC-23),
1,1,2,2-tetrafluoroethane (HFC-134),
1,1,1,2-tetrafluoroethane (HFC-134a),
pentafluoroethane (HFC-125),
1,1,1-trifluoroethane (HFC-143a),
1,1-difluoroethane (HFC-152a),
ethoxy-nonafluorobutane (HFE 7200),
trans-1,3,3,3-tetrafluoropropene (HFO-1234ze), cyclic, branched, or linear completely methylated siloxanes, the following classes of perfluorocarbons:
 1. cyclic, branched, or linear, completely fluorinated alkanes;
 2. cyclic, branched, or linear, completely fluorinated ethers with no unsaturations;
 3. cyclic, branched, or linear, completely fluorinated tertiary amines with no unsaturations; and
 4. sulfur-containing perfluorocarbons with no unsaturations and with the sulfur bonds to carbon and fluorine, and (B) the following low-reactive organic compounds which have been exempted by the U.S. EPA:
acetone,
ethane,
methyl acetate,
parachlorobenzotrifluoride (1-chloro-4-trifluoromethyl benzene),
perchloroethylene (tetrachloroethylene).

In other illustrative embodiments, the first organic solvent may include one or more VOCs, for example, ethanol or isopropanol.

In illustrative embodiments, the water-based fragrance composition may include between about 5 and about 17 wt % of the first organic solvent. In other illustrative embodiments, the water-based fragrance composition may include between about 10 and about 17 wt % of the first organic solvent. In other illustrative embodiments, the output rate of the water-based fragrance composition is about 1 gram per hour, the first organic solvent is ethanol, and the water-based fragrance composition may include between about 10 and about 11 wt % ethanol. In other illustrative embodiments, the output rate of the water-based fragrance composition is about 1 gram per hour, the first organic solvent is isopropanol, and the water-based fragrance composition may include about 5 wt % isopropanol. In other illustrative embodiments, the output rate of the water-based fragrance composition is about 1 gram per hour, the first organic solvent is acetone, and the water-based fragrance composition may include about 5 wt % acetone. In any of the preceding embodiments, the output rate of the water-based fragrance composition may alternatively be up to about 2 grams per hour.

The second organic solvent is a component of the water-based fragrance composition that includes a moderately volatile water soluble organic compound or multiple such compounds. When calculating desirable ranges for the water-based fragrance composition, all of the moderately volatile water soluble organic compound or compounds present in the water-based fragrance composition are considered part of the second organic solvent. In illustrative embodiments, the second organic solvent may have a boiling point greater than or equal to about 100° C. and less than or equal to about 300° C. Additionally, each of the moderately volatile water soluble organic compounds of the second organic solvent are defined as moderately volatile because each compound has a boiling point greater than or equal to about 100° C. and less than or equal to about 300° C.

In illustrative embodiments, the second organic solvent may be one or more moderately volatile water soluble organic compounds selected from polyhydric alcohols (including glycols), glycol ethers, glycol ether esters, sulfoxides, ethers, polyethers, cyclic ethers, lactones, carbonates, carboxylic acids, and the like, or combinations thereof. In illustrative embodiments, the second organic solvent may not be a VOC. In illustrative embodiments, the second organic solvent may include one or more of dipropylene glycol; propylene glycol; 1,2-hexanediol; dipropylene glycol methyl ether acetate; propylene glycol monopropyl ether; diethylene glycol monobutyl ether; or ethylene glycol monohexyl ether. In other illustrative embodiments, the second solvent may be a VOC, a non-VOC, or combinations thereof. Non-limiting examples of VOCs that are moderately volatile water soluble organic compounds include dipropylene glycol methyl ether; propylene glycol methyl ether; pentylene glycol; caprylyl glycol; propylene glycol methyl ether acetate; ethylene glycol mono n-propyl ether; propylene glycol monoethyl ether; dimethoxymethane; acetonitrile; dimethylsulfoxide; and combinations thereof. The current status of a solvent to determine whether or not it is a VOC should be checked and confirmed, as VOC lists change periodically, and no guarantees are made for the accuracy of the current VOC status as set by the California Environmental Protection Agency's Air Resources Board. In illustrative embodiments, the water-based fragrance composition includes between about 0 and about 22 wt % of the second organic solvent. In further illustrative embodiments, the water-based fragrance compositions includes between about 0 and about 17 wt % of the second organic solvent.

In illustrative embodiments, the water-based fragrance composition does not include a material with a boiling point greater than about 300° C. Solvents may be selected to solubilize 5 wt % or less of one or more fragrance without the inclusion of a material with a boiling point greater than about 300° C. In such embodiments, if the water-based fragrance composition includes more than one fragrance formulation, the total weight percentage of all fragrances is 5 wt % or less. In other illustrative embodiments, the solvents may be selected to solubilize 3 wt % or less of one or more fragrance formulations without the inclusion of any material with a boiling point greater than about 300° C. In such embodiments, if the water-based fragrance composition includes more than one fragrance, the total weight percentage of all the fragrance is about 3 wt % or less.

In an illustrative embodiment, the water-based fragrance composition comprises 11 wt % ethanol for the first organic solvent. In other illustrative embodiments, the water-based fragrance may comprise one or more of ethanol, isopropanol, or acetone.

In an illustrative embodiment, the second organic solvent comprises dipropylene glycol (DPG). In another illustrative embodiment, the second organic solvent comprises propylene glycol (PG). In another illustrative embodiment, the second organic solvent comprises 1,2-hexanediol. In another illustrative embodiment, the second organic solvent comprises dipropylene glycol methyl ether acetate (DPMA). In a further illustrative embodiment, the second organic solvent comprises propylene glycol methyl ether acetate (PMA). In an illustrative embodiment, the second organic solvent comprises propylene glycol methyl ether (PM). In an illustrative embodiment, the second organic solvent comprises Dimethoxymethane. In an illustrative embodiment, the second organic solvent comprises dipropylene glycol methyl ether (DPM). In another non-limiting, illustrative embodiment, the second organic solvent comprises about 12 wt % of Acetonitrile and about 10 wt % of Propylene Glycol n-Propyl Ether.

According to a further illustrative embodiment, a method of providing a long-lasting scent comprises the step of delivering boluses of droplets into air, wherein a vibrating mesh nebulizer or atomizing assembly 154 converts a liquid water-based fragrance composition into the droplets. The liquid water-based fragrance composition may comprise: a) at least about 70 wt % water; b) between about 5 and about 17 wt % of a first organic solvent, wherein the first organic solvent comprises of one or more relatively volatile, water soluble, low molecular weight organic compound(s) having a boiling point less than about 100° C., wherein the relatively volatile, water soluble, low molecular weight organic compound(s) is selected from the group consisting of alcohols, ethers, ketones, esters, and combinations thereof; c) about 5 wt % or less fragrance; and d) between about 0 and about 22 wt % of a second organic solvent. The second organic solvent may comprise of one or more moderately volatile water soluble organic compound(s) having a boiling point greater than or equal to about 100° C. and less than or equal to about 300° C. The moderately volatile water soluble organic compound(s) may be selected from the group consisting of polyhydric alcohols (including glycols), glycol ethers, glycol ether esters, ethers, polyethers, cyclic ethers, lactones, carbonates, carboxylic acids, sulfoxides, and combinations thereof.

While the reservoirs disclosed herein are described as including a wick, the methods and devices of the present application may be utilized with reservoirs that do not include a wick. In other words, any suitable reservoir(s) that includes any suitable feature or component to move volatile material to the atomizing assembly may be utilized.

Volatile materials for use with the atomizer devices of the present disclosure are described in greater detail in U.S. Application Ser. No. 62/194,653, filed Jul. 20, 2015, and entitled "Water-based Fragrance Composition, Fragrance Delivery Device, and Method of Providing a Long-lasting Scent".

Any of the embodiments described herein may be modified to include any of the structures or methodologies disclosed in connection with other embodiments.

All documents cited in the Detailed Description are, in relevant part, incorporated herein by reference; the citation of any document is not to be construed as an admission that it is prior art with respect to the present invention.

INDUSTRIAL APPLICABILITY

The present disclosure provides water-based fragrance compositions, devices for emission of water-based fragrance compositions, and methods for emitting long-lasting scent. The water-based fragrance compositions generally include an increased amount of water, which allows for continuous emission, if desired. The water-based fragrance compositions may also be free of materials with a boiling point greater than about 300 degrees C.

Numerous modifications to the present disclosure will be apparent to those skilled in the art in view of the foregoing description. Accordingly, this description is to be construed as illustrative only and is presented for the purpose of enabling those skilled in the art to make and use the embodiments of the present disclosure and to teach the best mode of carrying out same. The exclusive rights to all modifications which come within the scope of the appended claims are reserved.

We claim:

1. A volatile material atomizing device comprising:
a housing including an upper surface, a fan, a fluid outlet, a plurality of air inlets and a plurality of air outlets, wherein the plurality of air outlets are positioned at least partially around the fluid outlet, wherein the plurality of air outlets includes at least two air outlets spaced apart between 90 and 180 degrees about the fluid outlet and are configured for air flow to travel therethrough, an edge of at least one of the plurality of air outlets extending along and entirely within an air plane so that a central axis of the at least one air outlet is perpendicular to the air plane, the air plane being defined by the upper surface, and an edge of the fluid outlet extending along a fluid plane that is parallel to the air plane, the fluid plane being vertically offset and above the air plane;
a fluid reservoir, wherein the fluid reservoir is disposed within the housing;
a volatile material contained within the fluid reservoir; and
an atomizer in fluid communication with the fluid reservoir and positioned in the housing and configured to dispense the volatile material out of the housing, through the fluid outlet,
wherein the plurality of air outlets connect to an air channel defined in the housing, the housing being configured so that the air channel is isolated from the atomizer and the volatile material within the housing, from the fan to the air outlets, and
wherein the air flow out of the air outlets forms a partial column of air around the dispensed volatile material.

2. The volatile material atomizing device of claim 1, wherein the volatile material is a water-based fragrance composition comprising at least 70 wt % water.

3. The volatile material atomizing device of claim 2, wherein the water-based fragrance composition includes a first organic solvent, at least one fragrance formulation, and a second organic solvent.

4. The volatile material atomizing device of claim 3, wherein the first organic solvent is between 5 and 17 wt % and the second organic solvent is between 0 and 22 wt % of the water-based fragrance composition.

5. The volatile material atomizing device of claim 4, wherein the at least one fragrance formulation is 5 wt % or less of the water-based fragrance composition.

6. The volatile material atomizing device of claim 5, wherein the first organic solvent, the at least one fragrance formulation, and the second organic solvent form a homogenous liquid phase.

7. The volatile material atomizing device of claim 1, wherein the fan produces an air flow out of the plurality of air outlets greater than 4 cubic feet per minute (CFM).

8. The volatile material atomizing device of claim 7, wherein the atomizer produces a mist of fluid particles out of the fluid outlet, and wherein the air flow out of the plurality of air outlets and the mist of fluid particles out of the fluid outlet each exit the housing separately.

9. The volatile material atomizing device of claim 1, further including at least one sensor for identifying the fluid reservoir or the volatile material contained within the fluid reservoir.

10. A volatile material atomizing device comprising:
a housing including an upper surface, a fan, a fluid outlet defining a central axis, at least one air inlet, and a plurality of air outlets positioned at least partially around the fluid outlet, wherein the plurality of air outlets includes at least two air outlets positioned on opposing sides of the fluid outlet, the plurality of air outlets extending along air axes that are parallel to the central axis of the fluid outlet, and an edge of at least one of the plurality of air outlets being disposed entirely within a plane defined by the upper surface;
a fluid reservoir positioned within the housing, including a wick positioned within the fluid reservoir so that the plane is disposed between the fluid outlet and the wick;
a volatile material comprising a water-based fragrance composition and being contained within the fluid reservoir; and
an atomizer in fluid communication with the wick and positioned in the housing and configured to dispense the volatile material out of the housing, through the fluid outlet,
wherein the plurality of air outlets connect to an air channel defined in the housing, the housing being configured so that the air channel is isolated from the volatile material in the housing, from the fan to the air outlets, wherein the atomizer emits volatilized water-based fragrance composition out the fluid outlet, and the fan produces an airflow through the air channel and out the air outlets to form a partial column of air around the volatilized water-based fragrance composition to carry the volatilized water-based fragrance composition up and away from the atomizing device.

11. The volatile material atomizing device of claim 10, wherein an airflow produced by the fan is at least 4 cfm.

12. The volatile material atomizing device of claim 11, wherein the atomizer produces a mist of fluid particles out of the fluid outlet, and wherein the airflow and the mist mix outside the housing to reach a height of at least 4 feet above the housing.

13. The volatile material atomizing device of claim 10 further including at least one sensor for identifying the fluid reservoir or the volatile material contained within the reservoir.

14. The volatile material atomizing device of claim 10, wherein the water-based fragrance composition comprises at least 70 wt % water.

15. The volatile material atomizing device of claim 11, wherein the water-based fragrance composition further comprises a first organic solvent, at least one fragrance formulation, and a second organic solvent.

* * * * *